(12) United States Patent
Fujii et al.

(10) Patent No.: US 10,647,811 B2
(45) Date of Patent: May 12, 2020

(54) COPOLYMER, POLYMER, MOLDING MATERIAL AND RESIN MOLDED BODY

(71) Applicant: ZEON CORPORATION, Chiyoda-ku, Tokyo (JP)

(72) Inventors: Kensaku Fujii, Tokyo (JP); Takashi Houkawa, Tokyo (JP); Takuya Komatsubara, Tokyo (JP); Yasuhiro Shimizu, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 12 days.

(21) Appl. No.: 15/562,572

(22) PCT Filed: Apr. 5, 2016

(86) PCT No.: PCT/JP2016/061174
§ 371 (c)(1),
(2) Date: Sep. 28, 2017

(87) PCT Pub. No.: WO2016/163371
PCT Pub. Date: Oct. 13, 2016

(65) Prior Publication Data
US 2018/0086877 A1  Mar. 29, 2018

(30) Foreign Application Priority Data

Apr. 6, 2015 (JP) .................................. 2015-077411
Sep. 28, 2015 (JP) .................................. 2015-190477
Dec. 17, 2015 (JP) .................................. 2015-245878

(51) Int. Cl.
*C08F 232/04* (2006.01)
*C08G 61/08* (2006.01)
(Continued)

(52) U.S. Cl.
CPC ................ *C08G 61/08* (2013.01); *C08F 8/04* (2013.01); *C08F 132/08* (2013.01);
(Continued)

(58) Field of Classification Search
CPC ....... C08G 61/08; C08F 232/00; C08F 232/04
See application file for complete search history.

(56) References Cited

U.S. PATENT DOCUMENTS 5,635,573 A * 6/1997 Harrington ........... C08F 232/00
526/170
10,246,582 B2 * 4/2019 Sawaguchi ............. C08L 45/00
(Continued)

FOREIGN PATENT DOCUMENTS

CN       1464982 A     12/2003
JP    H07179575 A      7/1995
(Continued)

OTHER PUBLICATIONS

Jun. 21, 2016, International Search Report issued in the International Patent Application No. PCT/JP2016/061174.
(Continued)

*Primary Examiner* — Michael L Leonard
(74) *Attorney, Agent, or Firm* — Kenja IP Law PC

(57) ABSTRACT

The present invention provides: a copolymer (A) which is a copolymer obtained by copolymerizing one or plural cycloolefin monomers and one or plural acyclic olefin monomers, or by copolymerizing two or more cycloolefin monomers, wherein a glass transition temperature (Tg) is 100° C. or higher, a refractive index is 1.545 or higher, and an Abbe's number is 50 or larger; a polymer (B) selected from: a ring-opening homopolymer obtained by ring-opening polymerization of only a monomer represented by formula (I), a ring-opening copolymer obtained by ring-
(Continued)

opening copolymerization of the monomer represented by formula (I) and a monomer capable of ring-opening copolymerization with the monomer represented by formula (I), a hydrogenated product of the ring-opening homopolymer and a hydrogenated product of the ring-opening copolymer; a forming material containing the copolymer (A) or the polymer (B); and a resin formed article obtained by forming the forming material.

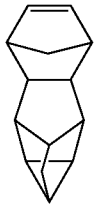

(I)

3 Claims, 3 Drawing Sheets

(51) Int. Cl.
| | |
|---|---|
| C08F 220/18 | (2006.01) |
| C08F 232/08 | (2006.01) |
| C08F 132/08 | (2006.01) |
| C08F 8/04 | (2006.01) |
| C08F 4/6592 | (2006.01) |
| C07C 13/64 | (2006.01) |
| G01N 25/48 | (2006.01) |
| G01R 33/46 | (2006.01) |

(52) U.S. Cl.
CPC .......... *C08F 220/18* (2013.01); *C08F 232/04* (2013.01); *C08F 232/08* (2013.01); *C07C 13/64* (2013.01); *C08F 4/6592* (2013.01); *C08G 2261/122* (2013.01); *C08G 2261/3325* (2013.01); *C08G 2261/418* (2013.01); *C08G 2261/60* (2013.01); *C08G 2261/62* (2013.01); *G01N 25/4866* (2013.01); *G01R 33/46* (2013.01)

(56) References Cited

U.S. PATENT DOCUMENTS

| 2003/0179460 A1 | 9/2003 | Kuroda et al. | |
|---|---|---|---|
| 2011/0077372 A1 | 3/2011 | Sakurai et al. | |
| 2013/0131212 A1* | 5/2013 | Mochizuki | C08F 220/18 522/107 |
| 2015/0346386 A1* | 12/2015 | Sato | G02B 1/041 524/81 |

FOREIGN PATENT DOCUMENTS

| JP | 2008144013 A | 6/2008 |
|---|---|---|
| JP | 2008174679 A | 7/2008 |
| JP | 2010511072 A | 4/2010 |
| JP | 2011068805 A | 4/2011 |
| JP | 2012046726 A | 3/2012 |
| TW | 201430004 A | 8/2014 |
| WO | 2008066305 A1 | 6/2008 |

OTHER PUBLICATIONS

Laura R. Gilliom et al., "Titanacyclobutanes Derived from Strained Cyclic Olefins: The Living Polymerization of Norbornene", Journal of the American Chemical Society, Feb. 1986, pp. 733-742, 108 (4).
Nancy Acton et al., "Dimerization and Trimerization of Norbornadiene by Soluble Rhodium Catalysts", Journal of the American Chemical Society, Jul. 26, 1972, pp. 5446-5456, 94 (15).
Nataliya F.Gol'dshleger et al., "Selective rhodium-containing zeolite catalysts for cyclodimerization of bicyclo [2.2.1]hepta-2,5-diene", Journal of Molecular Catalysis A: Chemical, Mar. 1996, pp. 159-168, vol. 106.
Peter Schwab et al., "Synthesis and Applications of RuCl2(= CHR')(PR3)2: The Influence of the Alkylidene Moiety on Metathesis Activity", Journal of the American Chemical Society, Jan. 10, 1996, pp. 100-110, 118 (1).
Sonbinh T. Nguyen et al., "Syntheses and Activities of New Single-component, Ruthenium-Based Olefin Metathesis Catalysts", Journal of the American Chemical Society, Oct. 1993, pp. 9858-9859, 115 (21).
S. Muthukumaru Pillai et al., "Cyclodimerization of 2,5-norbornadiene catalyzed by the Fe(acac)3-PPh3-Et2AlCl system +", New J. Chem., 1996, pp. 677-683, vol. 20.
Jan. 21, 2020, Notification of Reasons for Refusal issued by the Japan Patent Office in the corresponding Japanese Patent Application No. 2017-510998.

* cited by examiner

COPOLYMER, POLYMER, MOLDING MATERIAL AND RESIN MOLDED BODY

TECHNICAL FIELD

The present invention relates to a novel copolymer having a high glass transition temperature (Tg), a high refractive index and a high Abbe's number, a forming material containing the copolymer, and a resin formed article obtained by forming the forming material. In addition, the present invention relates to a polymer useful as a resin component of an optical formed article, a forming material containing the polymer, and a resin formed article obtained by forming the forming material.

BACKGROUND ART

Since polymers having repeating units derived from a cycloolefin monomer are excellent in transparency, low hygroscopicity, heat resistance, insulation property, chemical resistance and the like, they have been broadly utilized as forming materials for optical members and the like such as optical lenses.

For example, Patent Literature 1 describes an addition copolymer of a norbornene-based monomer and ethylene. Further, this literature also discloses a copolymer of 1,4-methano-1,4,4a-9a-tetrahydrofluorene (MTF) and ethylene in Examples. This copolymer has a high glass transition temperature (Tg) and a high refractive index, and is useful as a resin component of an optical formed article.

In addition, the resin component of the optical formed article such as a lens requires excellent transparency. From this viewpoint, poly(methyl methacrylate), polycarbonate, diethylene glycol bisallyl carbonate, poly(cyclohexyl methacrylate), poly(4-methylpentene), amorphous alicyclic polyolefin, polycyclic norbornene polymer, a vinyl alicyclic hydrocarbon polymer and the like have conventionally been used as resin components of optical formed articles. For example, Patent Literature 2 describes an optical formed article obtained by using a forming material containing a polycyclic norbornene polymer having a specific repeating unit.

In recent years, lenses for mobile phone cameras and the like are required to be further thinner and to have enhanced resolution. Thus, a resin having not only excellent transparency but also high refractive index and low birefringence has been required.

CITATION LIST

Patent Literature

Patent Literature 1: JP-A-2008-144013
Patent Literature 2: JP-A-2008-174679

SUMMARY OF INVENTION

Technical Problem

By using a cycloolefin monomer having an aromatic ring such as MTF like the copolymer described in Patent Literature 1, a polymer having a high glass transition temperature and a high refractive index can be easily obtained. However, since a polymer having an aromatic ring in its molecule tends to have a lower Abbe's number, a polymer having a high glass transition temperature (Tg), a high refractive index and a high Abbe's number was hardly obtained by introducing an aromatic ring.

The present invention was achieved in view of the above circumstances, and the first object of the present invention is to provide a novel copolymer having a high glass transition temperature (Tg), a high refractive index and a high Abbe's number, which is useful as a resin component of an optical formed article, a forming material containing the copolymer, and a resin formed article obtained by forming the forming material.

In addition, the second object of the present invention is to provide a polymer useful as a resin component of an optical formed article, a forming material containing the polymer, and a resin formed article obtained by forming the forming material.

Solution to Problem

In order to solve the above problem, the inventors conducted extensive studies with regard to a polymer having a repeating unit derived from a cycloolefin monomer. As a result, the inventors have found that a copolymer having a high glass transition temperature (Tg), a high refractive index and a high Abbe's number can be obtained by copolymerizing a cycloolefin monomer appropriately in combination with an acyclic olefin monomer or by copolymerizing two or more cycloolefin monomers appropriately in combination, and that a resin having excellent transparency, and furthermore a high refractive index and a low birefringence can be obtained by using a monomer represented by formula (I) described below as a cycloolefin monomer. These findings have led to the completion of the present invention.

Thus, one aspect of the invention provides a copolymer (A) of [1] to [7], a polymer (B) of [7] to [13], a forming material of [14] and [15], and a resin formed article of [16] described below.

[1] A copolymer (A), which is a copolymer obtained by copolymerizing one or plural cycloolefin monomers and one or plural acyclic olefin monomers, or a copolymer obtained by copolymerizing two or more cycloolefin monomers, wherein a glass transition temperature (Tg) is 100° C. or higher, a refractive index is 1.545 or higher, and an Abbe's number is 50 or larger.

[2] The copolymer (A) according to [1], wherein a ratio of the number of carbon atoms to the number of hydrogen atoms (number of carbon atoms/number of hydrogen atoms) in at least one of the cycloolefin monomers is 0.65 to 1.00.

[3] The copolymer (A) according to [1] or [2], wherein at least one of the cycloolefin monomers is a norbornene-based monomer.

[4] The copolymer (A) according to any one of [1] to [3], wherein at least one of the cycloolefin monomers is a deltacyclene.

[5] The copolymer (A) according to any one of [1] to [4], wherein at least one of the cycloolefin monomers is a monomer represented by the following formula (I).

[6] The copolymer (A) according to any one of [1] to [5], wherein at least one of the acyclic olefin monomers is an α-olefin-based monomer having 2 to 18 carbon atoms.

[7] The copolymer (A) according to any one of [1] to [6], wherein at least one of the acyclic olefin monomers is ethylene.

[8] A polymer (B) selected from: a ring-opening homopolymer obtained by ring-opening polymerization of only a monomer represented by the following formula (I);

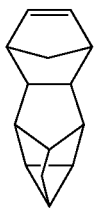

(I)

a ring-opening copolymer obtained by ring-opening copolymerization of the monomer represented by the above formula (I) and a monomer capable of ring-opening copolymerization with the monomer represented by the above formula (I); a hydrogenated product of the ring-opening homopolymer; and a hydrogenated product of the ring-opening copolymer.

[9] The polymer (B) according to [8], wherein the monomer capable of ring-opening copolymerization with the monomer represented by the above formula (I) is a compound represented by the following formula (II).

(II)

[10] The polymer (B) according to [8] or [9], wherein a refractive index ($n_d$) is 1.540 or higher.

[11] The polymer (B) according to any one of [8] to [10], wherein a birefringence (δn) per a unit thickness is −100 to +100.

[12] The polymer (B) according to any one of [8] to [11], wherein no melting point is observed, when a measurement sample obtained by melting and subsequent cooling is subjected to DSC measurement while heating it to 350° C. at an increase rate of 10° C./min.

[13] The polymer (B) according to any one of [8] to [12], wherein a glass transition temperature is 120 to 180° C.

[14] A forming material containing the copolymer (A) according to any one of [1] to [7] or the polymer (B) according to any one of [8] to [13].

[15] The forming material according to [14], wherein no melting point is observed when carrying out DSC measurement.

[16] A resin formed article obtained by forming the forming material according to [14] or [15].

Advantageous Effects of Invention

One aspect of the invention provides a novel copolymer [A] having a high glass transition temperature (Tg), a high refractive index and a high Abbe's number, which is useful as a resin component of an optical formed article, a forming material containing the copolymer [A], and a resin formed article obtained by forming the forming material.

In addition, one aspect of the invention provides a polymer [B] useful as a resin component of an optical formed article, a forming material containing the polymer [B], and a resin formed article obtained by forming the forming material.

DESCRIPTION OF EMBODIMENTS

Figure 1:
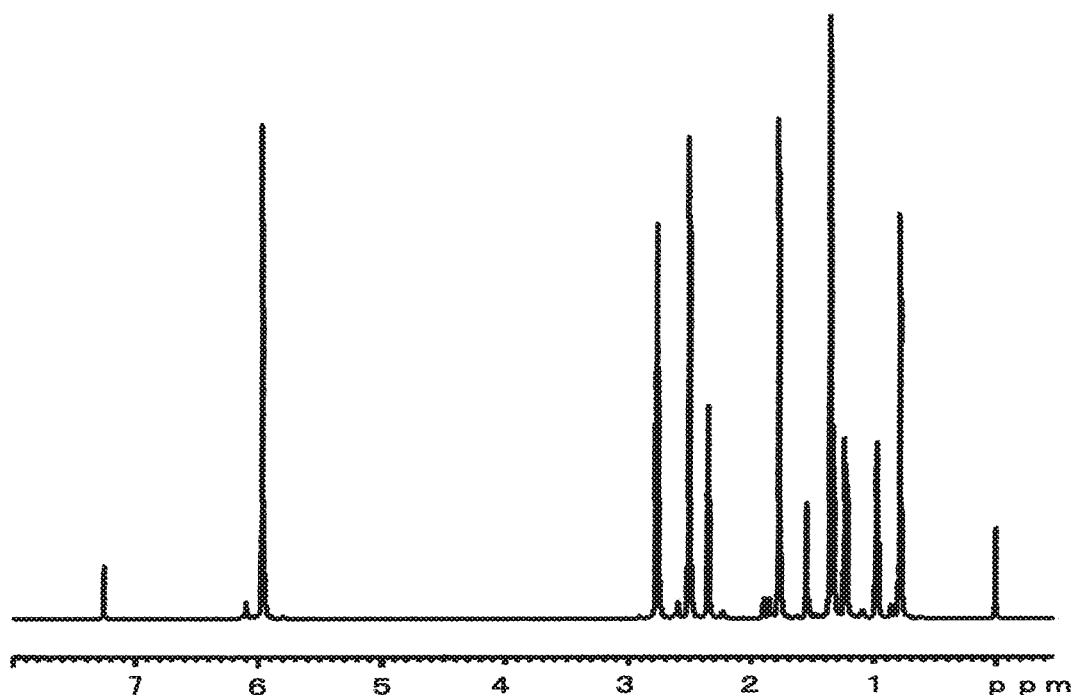
FIG. 1 illustrates a $^1$H-NMR chart (without integral representation) of a monomer (5). The abscissa represents values of chemical shift (ppm), and the ordinate represents peak intensities.

Hereinafter, the present invention is classified into 1) copolymer (A), 2) polymer (B), 3) forming material and 4) resin formed article, and described in detail.

1) Copolymer (A)

The copolymer (A) according to one embodiment of the invention is a copolymer obtained by copolymerizing one or plural cycloolefin monomers and one or plural acyclic olefin monomers or a copolymer obtained by copolymerizing two or more cycloolefin monomers, wherein a glass transition temperature (Tg) is 100° C. or higher, a refractive index is 1.545 or higher, and an Abbe's number is 50 or larger.

Hereinafter, among the copolymers (A) according to one embodiment of the invention, the copolymer obtained by copolymerizing one or plural cycloolefin monomers and one or plural acyclic olefin monomers is referred to as "copolymer (AI)", and the copolymer obtained by copolymerizing two or more cycloolefin monomers is referred to as "copolymer (AII)" in some cases.

[Monomer]

The cycloolefin monomer used for producing the copolymer (AI) or the copolymer (AII) is a compound having a ring structure composed of carbon atoms and including carbon-carbon double bonds on the ring. Specifically, it is exemplified by a monocyclic cycloolefin monomer and a norbornene-based monomer.

Examples of the monocyclic cycloolefin monomer include a cyclic monoolefin such as cyclobutene, cyclopentene, methylcyclopentene, cyclohexene, methylcyclohexene, cycloheptene and cyclooctene; a cyclic diolefin such as cyclohexadiene, methylcyclohexadiene, cyclooctadiene, methylcyclooctadiene and phenylcyclooctadiene; and the like.

The term "norbornene-based monomer" refers to a monomer which includes a norbornene ring.

Examples of the norbornene-based monomer include a bicyclic monomer such as bicyclo[2.2.1]hept-2-ene (trivial name: norbornene), 5-ethylidene-bicyclo[2.2.1]hept-2-ene (trivial name: ethylidenenorbornene) and a derivative thereof (which includes a substituent on the ring); a tricyclic monomer such as tricyclo[4.3.0.1$^{2,5}$]deca-3,7-diene (trivial name: dicyclopentadiene) and a derivative thereof; a tetracyclic monomer such as 7,8-benzotricyclo[4.3.0.1$^{2,5}$]deca-3-ene (trivial name: methanotetrahydrofluorene, also referred to as "tetracyclo[7.4.0.0$^{2,7}$.1$^{10,13}$]trideca-2,4,6,11-tetraene), tetracyclo[4.4.0.1$^{2,5}$.1$^{7,10}$]dodeca-3-ene (trivial name: tetracyclododecene), 8-ethylidenetetracyclo [4.4.0.1$^{2,5}$.1$^{7,10}$]-3-dodecene and a derivative thereof; a monomer having not less than 5 rings such as 1,2,3,3a,4,6a-hexahydro-1,2,4-methenopentalene (trivial name: deltacyclene), 1,2,3,3a,3b,4,7,7a,8,8a-decahydro-4,7-methano-2,3,8-metheno cyclopent[a]indene (the monomer represented by the above formula (I), hereinafter referred to as "MMD" in some cases) and a derivative thereof; and the like.

The MMD can be synthesized by reactions represented by e.g. the following formulas (α) and (β).

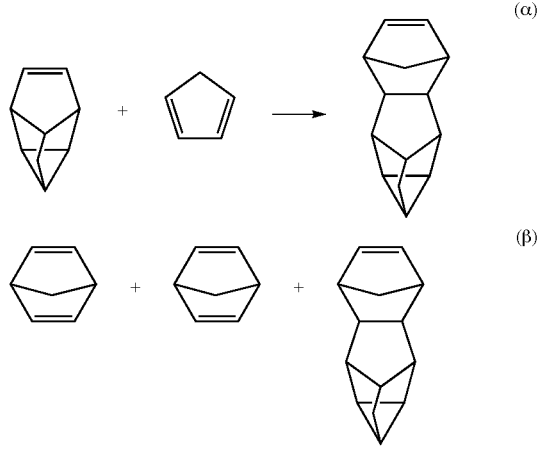

The reaction represented by the formula (α) (hereinafter, this reaction is referred to as "reaction (α)" in some cases) is a general Diels-Alder reaction, for which known reaction conditions can be utilized. In addition, the reaction represented by the formula (β) (hereinafter, this reaction is referred to as "reaction (β)" in some cases) can be carried out in accordance with a method described in Polymer Bulletin 18, 203-207 (1987), Journal of Catalyst 258, 5-13 (2008), J. Am. Chem. Soc. 1972, 94, 5446 or the like.

Specifically, the MMD can be synthesized by the reaction (α) or the reaction (β) when the reaction is carried out at 0 to 300° C. in the presence or absence of a solvent. At this time, a catalyst may be used as required.

Examples of the solvent include an aromatic hydrocarbon-based solvent such as benzene, toluene and xylene; an aliphatic hydrocarbon-based solvent such as pentane and hexane; an alicyclic hydrocarbon-based solvent such as cyclohexane and methylcyclohexane; an alcohol-based solvent such as methanol, ethanol, isopropanol and butanol; an ether-based solvent such as tetrahydrofuran, diethyl ether, dipropyl ether and 1,4-dioxane; an ester-based solvent such as ethyl acetate and propyl acetate; a halogen-containing compound-based solvent such as methylene chloride and chloroform; a nitrogen-containing compound-based solvent such as N-methylpyrrolidone; and the like.

The MMD includes 4 stereoisomers represented by the following formulas.

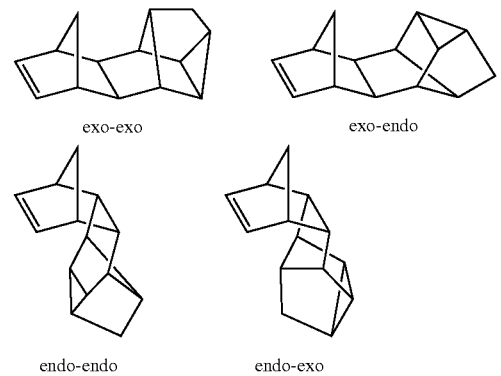

exo-exo    exo-endo endo-endo    endo-exo

It is known that when the MMD is synthesized by the reaction (α), an endo-adduct (an endo-endo product or an endo-exo product) is preferentially produced by kinetic control (referred to as an endo rule).

When MMD is synthesized by the reaction (β), it is known that the ratio of the produced isomer varies depending on the reaction conditions. For example, there are reports that an exo-endo product is preferentially produced under the condition described in J. Am. Chem. Soc. 1972, 94, 5446, J. Mol. Catal. A. 1996, 106, 159, and that an endo-endo product is preferentially produced under the condition described in New. J. Chem. 1996, 20, 677.

Thus, although some of the norbornene-based monomers include stereoisomers, all of these stereoisomers can be used as monomers in the present invention. In addition, as a monomer, one isomer may be used alone, or alternatively an isomer mixture including two or more isomers in an arbitrary ratio may be used.

The above-described norbornene-based monomer may have a substituent at an arbitrary position. Examples of such a substituent include an alkyl group such as a methyl group and an ethyl group; an alkenyl group such as a vinyl group; an alkylidene group such as an ethylidene group and a propane-2-ylidene group; an aryl group such as a phenyl group; a hydroxy group; an acid anhydride group; a carboxyl group; an alkoxycarbonyl group such as a methoxycarbonyl group; and the like.

These cycloolefin monomers may be used either alone or in combination.

A ratio of the number of carbon atoms to the number of hydrogen atoms (number of carbon atoms/number of hydrogen atoms) in at least one of the cycloolefin monomers to be used is preferably 0.65 to 1.00, more preferably 0.66 to 0.95, and even more preferably 0.67 to 0.90. If the ratio is too low, the refractive index possibly decreases. On the other hand, if the ratio is too high, the Abbe's number ($v_d$) possibly decreases.

The cycloolefin monomer satisfying the above ratio is preferably a norbornene-based monomer, more preferably a monomer having 5 or more rings, and even more preferably a deltacyclene or an MMD, because a polymer having a high glass transition temperature (Tg), a high refractive index and a high Abbe's number can be easily obtained.

The acyclic olefin monomer used for producing the copolymer (AI) is a compound having a polymerizable carbon-carbon double bond in its molecule (with the proviso of excluding cycloolefin monomers). The acyclic olefin monomer may be linear or branched, or may have a ring structure. Further, the acyclic olefin monomer may be an α-olefin or an internal olefin.

The acyclic olefin monomer can be used either alone or in combination.

At least one of the acyclic olefins to be used is preferably an α-olefin-based monomer having 2 to 18 carbon atoms, and more preferably 2 to 10 carbon atoms.

Examples of such an α-olefin monomer include ethylene; α-olefin such as propylene, 1-butene, isobutene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, 2-vinylnorbornane, 3-vinyltetracyclo[4.4.0.1$^{2,5}$.1$^{7,10}$]dodecane; and the like. Above all, ethylene is preferred.

[Copolymer (A)]

A copolymer (A) according to one embodiment of the invention is a copolymer obtained by copolymerizing one or plural cycloolefin monomers and one or plural acyclic olefin monomers or a copolymer obtained by copolymerizing two or more cycloolefin monomers, wherein a glass transition temperature (Tg) is 100° C. or higher, a refractive index is 1.545 or higher, and an Abbe's number is 50 or larger.

The copolymer (A) according to one embodiment of the invention is normally a polymer having an alicyclic structure in its molecule.

Examples of the alicyclic structure contained in the copolymer (A) according to one embodiment of the invention include a cycloalkane structure and a cycloalkene structure. Above all, a cycloalkane structure is preferred because a copolymer excellent in transparency, light resistance, durability and the like can be easily obtained. The number of carbon atoms constituting the alicyclic structure is not particularly limited, but is normally 4 to 30, preferably 5 to 20, and more preferably 5 to 15.

The weight average molecular weight (Mw) of the copolymer (A) according to one embodiment of the invention is preferably 10,000 to 300,000, and more preferably 20,000 to 200,000. A strength of a resin formed article obtained by using a copolymer having a low weight average molecular weight (Mw) possibly decreases. On the other hand, if the weight average molecular weight (Mw) of the copolymer (A) is too high, the formability of the forming material possibly decreases.

The molecular weight distribution (Mw/Mn) of the copolymer (A) according to one embodiment of the invention is not particularly limited, but is preferably 1 to 8, and more preferably 1 to 6.

When the molecular weight distribution of the copolymer (A) is within the above range, a resin formed article having a sufficient mechanical strength can be obtained.

The weight average molecular weight (Mw) and the number average molecular weight (Mn) of the copolymer (A) refer to standard polyisoprene-equivalent values determined by gel permeation chromatography (GPC) using cyclohexane as an eluent.

The copolymer (A) according to one embodiment of the invention is preferably a copolymer having a repeating unit derived from a cycloolefin monomer satisfying the ratio of the number of carbon atoms to the number of hydrogen atoms described above.

When the copolymer (A) according to one embodiment of the invention is the copolymer having the repeating unit derived from the cycloolefin monomer satisfying the ratio of the number of carbon atoms to the number of hydrogen atoms described above, the amount of such a repeating unit is preferably 60 wt % or more, more preferably 65 wt % or more, and even more preferably 70 wt % or more based on the whole repeating unit.

Among the copolymers (A) according to one embodiment of the invention, examples of the copolymer (AI) include a polymer obtained by addition copolymerization of one or plural of the cycloolefin monomers and one or plural of the acyclic olefin monomers, or a hydrogenated product hereof.

The copolymer (AI) may contain one or plural repeating units derived from a cycloolefin monomer. Further, it may contain one or plural repeating units derived from an acyclic olefin monomer.

The copolymer (AI) may be a block copolymer or a random copolymer.

The weight ratio of the repeating unit derived from the cycloolefin monomer to the repeating unit derived from the acyclic olefin monomer (repeating unit derived from the cycloolefin monomer:repeating unit derived from the acyclic olefin monomer) in the copolymer (AI) is preferably 85:15 to 15:85, and more preferably 70:30 to 30:70.

The method for producing the copolymer (AI) is not particularly limited. For example, the copolymer (AI) can be produced by a radical polymerization reaction, an anionic polymerization reaction, a cationic polymerization reaction, a coordination polymerization reaction or the like. Above all, the coordination polymerization reaction is preferred because the target addition copolymer can be obtained with a high yield.

The details of the reaction conditions in the coordination polymerization reaction are not particularly limited, and a conventionally known method can be appropriately utilized.

For example, the copolymer (AI) can be produced by polymerizing a cycloolefin monomer and an acyclic olefin monomer using a polymerization catalyst.

As the polymerization catalyst in the coordination polymerization reaction, a known polymerization catalyst for an addition polymerization reaction can be used. Examples of such a polymerization catalyst include a metallocene catalyst including a metallocene compound (a) containing a Group 4 metal atom, and an organoaluminumoxy compound (b), for example.

Examples of the metallocene compound (a) include a crosslinked metallocene compound, a half metallocene compound and a non-crosslinked half metallocene compound.

Examples of the crosslinked metallocene compound include, for example, a compound represented by the following formula (III).

(III)

In the formula (III), $M_1$ is a metal atom selected from a group consisting of titanium, zirconium and hafnium, where zirconium is preferred because of excellent catalytic activity.

Each of $X_1$ and $X_2$ independently represents an alkyl group having 1 to 6 carbon atoms or a halogen atom.

R₁ represents a divalent group. Examples of R₁ include an alkylene group having 1 to 5 carbon atoms such as a methylene group, an ethylene group, a trimethylene group and a propane-2,2-diyl group (isopropylidene group); a group having 1 to 5 silicon atoms such as silylene group and a disilylene group; and the like. They may have a substituent. Examples of R₁ having a substituent include a diphenylmethylene group, a dimethylsilylene group, a diphenylsilylene group, and the like.

Each of R₂ and R₃ independently represents a cyclopentadienyl group, an indenyl group or a fluorenyl group. These groups may have a substituent at an arbitrary position. Examples of such a substituent include an alkyl group having 1 to 10 carbon atoms such as a methyl group, an ethyl group, an isopropyl group and a t-butyl group; an aryl group having 6 to 12 carbon atoms such as a phenyl group; an arylalkyl group such as a benzyl group and a phenethyl group; and the like.

Examples of the compound represented by formula (III) include isopropylidene-(9-fluorenyl) (cyclopentadienyl) zirconium dichloride, isopropylidene-(9-fluorenyl)[1-(3-methyl)cyclopentadienyl] zirconium dichloride, isopropylidene-(9-fluorenyl)[1-(3-t-butyl)cyclopentadienyl] zirconium dichloride, isopropylidene-(1-indenyl) (cyclopentadienyl)zirconium dichloride, isopropylidene-bis(1-indenyl)zirconium dichloride, diphenylmethylene-(9-fluorenyl) (cyclopentadienyl)zirconium dichloride, diphenylmethylene-bis(1-indenyl)zirconium dichloride, ethylene-bis(1-indenyl)zirconium dichloride, dimethylsilylene-bis(1-indenyl) zirconium dichloride, and the like.

Examples of the half metallocene compound include, for example, a compound represented by the following formula (IV).

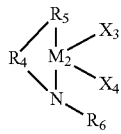

(IV)

In the formula (IV), M₂ is a metal atom selected from a group consisting of titanium, zirconium and hafnium, where zirconium is preferred because of excellent catalytic activity.

Each of X₃ and X₄ independently represents an alkyl group having 1 to 6 carbon atoms, or a halogen atom.

R₄ represents a divalent group. Examples of R₄ include the same groups as those indicated for R₁.

R₅ represents a cyclopentadienyl group, an indenyl group, or a fluorenyl group. These groups may have a substituent at an arbitrary position. Examples of such a substituent include an alkyl group having 1 to 10 carbon atoms such as a methyl group, an ethyl group, an isopropyl group and a t-butyl group; an aryl group having 6 to 12 carbon atoms such as a phenyl group; an arylalkyl group such as a benzyl group and a phenethyl group; and the like.

R₆ represents an alkyl group having 1 to 6 carbon atoms.

Examples of the compound represented by formula (IV) include (t-butyramide)dimethyl-1-indenyl silane titanium dimethyl, (t-butyramide)dimethyl-1-indenyl silane titanium dichloride, (t-butyramide)dimethyl-9-fluorenyl silane titanium dimethyl, (t-butyramide)dimethyl-9-fluorenyl silane titanium dichloride, (t-butyramide)dimethyl-9-(3,6-dimethylfluorenyl)silane titanium dimethyl, (t-butyramide)dimethyl-9-[3,6-di(isopropyl)fluorenyl]silane titanium dimethyl, (t-butyramide)dimethyl-9-[3,6-di(t-butyl)fluorenyl] silane titanium dimethyl, (t-butyramide)dimethyl-9-[2,7-di(t-butyl)fluorenyl]silane titanium dimethyl, (t-butyramide) dimethyl-9-(2,3,6,7-tetramethylfluorenyl) silane titanium dimethyl, and the like.

Examples of the non-crosslinked half metallocene compound include, for example, a compound represented by the following formula (V).

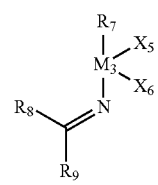

(V)

In the formula (V), M₃ is a metal atom selected from a group consisting of titanium, zirconium and hafnium, where zirconium is preferred because of excellent catalytic activity.

Each of X₅ and X₆ independently represents an alkyl group having 1 to 6 carbon atoms or a halogen atom.

R₇ represents a cyclopentadienyl group, an indenyl group or a fluorenyl group. These groups may have a substituent at an arbitrary position. Examples of such a substituent include an alkyl group having 1 to 10 carbon atoms such as a methyl group, an ethyl group, an isopropyl group and a t-butyl group; an aryl group having 6 to 12 carbon atoms such as a phenyl group; an arylalkyl group such as a benzyl group and a phenethyl group; and the like.

Each of R₈ and R₉ independently represents an alkyl group having 1 to 6 carbon atoms.

Examples of the compound represented by formula (V) include CpTi[N=C(t-Bu)₂]Cl₂, (t-BuCp)Ti[N=C(t-Bu)₂] Cl₂, CpTi[N=C(t-Bu)₂](CH₃)₂, (t-BuCp)Ti[N=C(t-Bu)₂] (CH₃)₂ and the like. In these formulas, "Cp" represents a group represented by R₆.

Above all, the compound represented by the above formula (V) is preferred as the metallocene compound (a) because of efficient copolymerization reaction.

The organoaluminumoxy compound (b) constituting the polymerization catalyst is an activator for activating the metallocene compound (a).

The organoaluminumoxy compound (b) may be a conventionally known aluminoxane or a benzene-insoluble organoaluminumoxy compound as disclosed in JP-A-2-78687.

The polymerization catalyst may contain an organoaluminum compound (c). The organoaluminum compound (c) is an organoaluminum compound other than the aluminumoxy compound (b). Examples of such an organoaluminum compound include a trialkylaluminum such as trimethylaluminum, triethylaluminum, triisopropylaluminum, tri-n-butylaluminum, triisobutylaluminum and tri-sec-butylaluminum; a dialkylaluminum halide such as dimethylaluminum chloride and diisobutylaluminum chloride; a dialkylaluminum hydride such as diisobutylaluminum hydride; a dialkylaluminum alkoxide such as dimethylaluminum methoxide; a dialkylaluminum aryloxide such as diethylaluminum phenoxide; and the like.

The concentration of the metallocene compound (a) at the start of the polymerization reaction is preferably 0.00005 to 1.0 mmol/L, and more preferably 0.0001 to 0.3 mmol/L. In addition, the amount of the organoaluminumoxy compound (b) is preferably 1 to 10,000 equivalents based on the metallocene compound (a). When the polymerization catalyst contains the organoaluminum compound (c), the amount of the organoaluminum compound (c) is preferably 0.1 to 1,000 equivalents based on the metallocene compound (a).

The polymerization reaction is normally effected in an organic solvent. The organic solvent is not particularly limited as long as it is inert to the polymerization reaction. Examples of the organic solvent to be used include an aromatic hydrocarbon-based solvent such as benzene, toluene and xylene; an aliphatic hydrocarbon-based solvent such as n-pentane, n-hexane and n-heptane; an alicyclic hydrocarbon-based solvent such as cyclohexane, methylcyclohexane, decalin and bicyclononane; a halogenated hydrocarbon-based solvent such as dichloroethane, chlorobenzene, dichlorobenzene and trichlorobenzene; and the like.

The polymerization temperature is normally −50 to 250° C., preferably −30 to 200° C., and more preferably −20 to 150° C. The polymerization time is appropriately selected depending on polymerization conditions, but is normally 30 minutes to 20 hours, and preferably 1 to 10 hours.

After the polymerization reaction, the addition copolymer according to one embodiment of the invention can be obtained by carrying out isolation and purification in accordance with an ordinary method.

By hydrogenation reaction of the copolymer obtained by the above-described method, the hydrogenated product thereof can be obtained.

This hydrogenation reaction can be effected by bringing the copolymer into contact with hydrogen under the presence of a hydrogenation catalyst in accordance with an ordinary method.

The hydrogenation catalyst may be a homogeneous catalyst or a heterogeneous catalyst.

Since a homogeneous catalyst is easily dispersed in a hydrogenation reaction solution, the amount of catalyst to be added can be reduced. In addition, since a homogeneous catalyst exhibits sufficient activity even when the temperature and the pressure are not increased, decomposition or gelation of the copolymer and a hydrogenated product thereof hardly occurs. Therefore, a homogeneous catalyst is preferably used from the viewpoint of cost and the quality of the product.

On the other hand, since a heterogeneous catalyst exhibits particularly excellent activity at a high temperature under a high pressure, the copolymer can be hydrogenated within a short time. Moreover, a catalyst residue can be efficiently removed after completion of the hydrogenation reaction.

Examples of the homogeneous catalyst include a Wilkinson's complex [chlorotris(triphenylphosphine)rhodium(I)]; a catalyst including a combination of a transition metal compound and an alkylmetal compound, such as combinations of cobalt acetate/triethylaluminum, nickel acetylacetonate/triisobutylaluminum, titanocene dichloride/n-butyllithium, zirconocene dichloride/sec-butyllithium, tetrabutoxytitanate/dimethylmagnesium and the like; and the like.

Examples of the heterogeneous catalyst include a catalyst in which a metal such as Ni, Pd, Pt, Ru and Rh is supported on a support. Particularly, when the amount of impurities in the resulting hydrogenated product is to be reduced, it is preferable to use an adsorbent such as alumina and diatomaceous earth as the support.

The hydrogenation reaction is normally effected in an organic solvent. The organic solvent is not particularly limited as long as it is inert to the hydrogenation reaction. As the organic solvent, a hydrocarbon-based solvent is normally used since it can easily dissolve the resulting hydrogenated product. Examples of the hydrocarbon-based solvent include an aromatic hydrocarbon-based solvent such as benzene, toluene and xylene; an aliphatic hydrocarbon-based solvent such as n-pentane, n-hexane and n-heptane; an alicyclic hydrocarbon-based solvent such as cyclohexane, methylcyclohexane, decalin and bicyclononane; and the like.

These organic solvents may be used either alone or in combination. In addition, a solvent used for a ring-opening polymerization reaction is normally also suitable as a solvent for a hydrogenation reaction, and therefore, after the hydrogenation catalyst is added to the ring-opening polymerization reaction solution, it can be subjected to the hydrogenation reaction.

The hydrogenation ratio varies depending on the type of hydrogenation catalyst and the reaction temperature. Therefore, when the copolymer has an aromatic ring, a residual ratio of the aromatic ring can be controlled by selection of the hydrogenation catalyst, adjustment of the reaction temperature or the like. For example, the unsaturated bonds of an aromatic ring can be allowed to remain to a certain extent or higher by controls such as decrease of the reaction temperature, lowering of the hydrogen pressure and reduction of the reaction time.

A catalyst residue can be removed by a treatment such as centrifugation and filtration after completion of the hydrogenation reaction. In addition, a catalyst deactivation agent such as water and alcohol may be used, or an adsorbent such as activated clay and alumina may be added, as required.

Among the copolymers (A) according to one embodiment of the invention, examples of the copolymer (AII) include a polymer obtained by addition copolymerization of two or more cycloolefin monomers (hereinafter referred to as "copolymer (AII-a)" in some cases) or a hydrogenated product thereof, and a polymer obtained by ring-opening copolymerization of two or more cycloolefin monomers (hereinafter referred to as "copolymer (AII-b)" in some cases) or a hydrogenated product thereof.

The copolymer (AII) may be either a block copolymer or a random copolymer.

The method for producing the copolymer (AII) is not particularly limited. For example, the copolymer (AII-a) can be produced by the same method as for producing the copolymer (AI) except that two or more cycloolefin monomers are used in combination instead of the combination of the cycloolefin monomer and the acyclic olefin monomer in the method described above as a method for producing the copolymer (AI).

In addition, the copolymer (AII-b) can be produced by ring-opening polymerization of two or more cycloolefin monomers in accordance with a known method using a metathesis polymerization catalyst.

The metathesis polymerization catalyst is not particularly limited. A known metathesis polymerization catalyst may be used. Examples of the metathesis polymerization catalyst include a catalyst system which includes a halide, a nitrate or an acetylacetone compound of a metal selected from ruthenium, rhodium, palladium, osmium, iridium, platinum and the like, and a reducing agent; a catalyst system which includes a halide or an acetylacetone compound of a metal selected from titanium, vanadium, zirconium, tungsten and molybdenum, and an organoaluminum compound as a cocatalyst; a Schrock-type or Grubbs-type living ring-opening metathesis polymerization catalyst (JP-A-7-179575, J. Am.

Chem. Soc., 1986, 108, p. 733, J. Am. Chem. Soc., 1993, 115, p. 9858, and J. Am. Chem. Soc., 1996, 118, p. 100); and the like.

These metathesis polymerization catalysts can be used either alone or in combination.

The amount of the metathesis polymerization catalyst to be used may be appropriately selected taking account of the polymerization conditions and the like, but is normally 0.000001 to 0.1 mol, and preferably 0.00001 to 0.01 mol based on 1 mol of the monomer.

A linear α-olefin having 4 to 40 carbon atoms such as 1-butene, 1-hexene and 1-decene can be used as a molecular weight modifier when subjecting the cycloolefin monomer to ring-opening polymerization.

The linear α-olefin is normally added in an amount of 0.001 to 0.030 mol, preferably 0.003 to 0.020 mol, and more preferably 0.005 to 0.015 mol based on 1 mol of the cycloolefin monomer.

The ring-opening polymerization of the cycloolefin monomer can be effected in an organic solvent. The organic solvent is not particularly limited as long as it is inert to the polymerization reaction. Examples of the organic solvent include an aromatic hydrocarbon-based solvent such as benzene, toluene and xylene; an aliphatic hydrocarbon-based solvent such as n-pentane, n-hexane and n-heptane; an alicyclic hydrocarbon-based solvent such as cyclohexane, methylcyclohexane, decalin and bicyclononane; a halogenated hydrocarbon-based solvent such as dichloroethane, chlorobenzene, dichlorobenzene and trichlorobenzene; and a mixed solvent which includes two or more of these solvents.

The polymerization temperature is not particularly limited, but is normally −50 to 250° C., preferably −30 to 200° C., and more preferably −20 to 150° C. The polymerization time is appropriately selected taking account of the polymerization conditions, but is normally 30 minutes to 20 hours, and preferably 1 to 10 hours.

A hydrogenated product of the ring-opening copolymer can be obtained by subjecting the ring-opening copolymer obtained in accordance with the above-described method to a hydrogenation reaction. The hydrogenation reaction of the ring-opening copolymer can be effected by bringing the ring-opening copolymer into contact with hydrogen under the presence of a hydrogenation catalyst in accordance with an ordinary method. Specifically, the hydrogenation reaction of the ring-opening copolymer can be effected in the same manner as the method described above in the explanation of the copolymer (AI).

The glass transition temperature (Tg) of the copolymer (A) according to one embodiment of the invention is 100° C. or higher, preferably 115 to 175° C., and more preferably 130 to 160° C. A copolymer having a glass transition temperature (Tg) of 100° C. or higher is preferably used as a resin component of a resin formed article having excellent heat resistance.

The glass transition temperature (Tg) of the copolymer (A) can be measured by the method described in Examples.

The refractive index ($n_d$) of the copolymer (A) according to one embodiment of the invention is 1.545 or higher, preferably 1.547 to 1.700, and more preferably 1.548 to 1.600. A copolymer having a refractive index ($n_d$) of 1.545 or higher is preferably used as a resin component of an optical formed article.

The refractive index ($n_d$) of the copolymer can be measured by the method described in Examples.

The Abbe's number of the copolymer (A) according to one embodiment of the invention is 50 or larger, preferably 53 to 60, and more preferably 54 to 58.

The Abbe's number means a value indicating a degree of the refractive index for each wavelength of light (wavelength dispersion of refractive index). When the refractive indexes of the materials to lights of F line (wavelength: 486.1 nm), d line (wavelength: 587.6 nm) and Cline (wavelength: 656.3 nm) of the Fraunhofer lines are defined as $n_F$, $n_d$ and $n_c$, respectively, the Abbe's number ($v_d$) is defined by the following equation (1).

$$v_d = (n_d - 1)/(n_F - n_c) \qquad (1)$$

The larger the Abbe's number ($v_d$) of the material is, the lower the wavelength dispersion of the refractive index is and the lower the unevenness of the light emission angles for respective wavelengths is. The smaller the Abbe's number of the material is, the higher the wavelength dispersion of the refractive index is and the higher the unevenness of the light emission angles for respective wavelengths is.

A copolymer having an Abbe number ($v_d$) of 50 or larger is preferably used as a raw material for producing a low-dispersion optical member.

Normally, a glass transition temperature and a refractive index of an obtained copolymer tend to increase by introducing an aromatic ring into its molecule, but an Abbe's number decreases. Thus, a copolymer having a high glass transition temperature (Tg), a high refractive index and a high Abbe's number is hardly obtained even by this method.

On the other hand, a copolymer having a high glass transition temperature (Tg), a high refractive index and a high Abbe's number can be efficiently obtained by appropriately utilizing a cycloolefin monomer having a polycyclic structure such as deltacyclene or MMD like the copolymer (A) according to one embodiment of the invention.

A birefringence (δn) per a unit thickness of the copolymer (A) according to one embodiment of the invention is preferably −100 to +100, more preferably −85 to +80, and particularly preferably −60 to +60.

A birefringence per a unit thickness can be measured by the method described in Examples.

In relation to the copolymer (AI) according to one embodiment of the invention, a copolymer having a higher glass transition temperature, a higher refractive index and a higher Abbe's number can be easily obtained by using a monomer having a large ratio of the number of carbon atoms to the number of hydrogen atoms such as deltacyclene and MMD as a cycloolefin monomer, or by using a monomer having a ring structure as an acyclic olefin monomer.

Additionally, in relation to the copolymer (AII) according to one embodiment of the invention, although a ring-opening copolymer tends to have a lower glass transition temperature and a lower refractive index than those of an addition copolymer, a copolymer having a sufficiently high glass transition temperature, a sufficiently high refractive index and a sufficiently high Abbe's number can be easily obtained by using a monomer having a large ratio of the number of carbon atoms to the number of hydrogen atoms such as deltacyclene and MMD as a monomer to be used.

2) Polymer (B)

The polymer (B) according to one embodiment of the invention is a ring-opening homopolymer obtained by ring-opening polymerization of only a monomer (MMD) represented by the following formula (I)

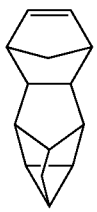

(I)

(hereinafter referred to as "polymer (α)" in some cases), a ring-opening copolymer obtained by ring-opening copolymerization of an MMD and a monomer capable of ring-opening copolymerization with the MMD (hereinafter referred to as "polymer (β)" in some cases), or a hydrogenated product thereof (hereinafter referred to as "polymer (γ)" in some cases).

A polymer having excellent transparency, a high refractive index and a low birefringence can be obtained by using the MMD as a monomer.

The MMD can be synthesized by the reactions (α) and (β).

As mentioned above, the MMD includes 4 stereoisomers represented by the following formulas.

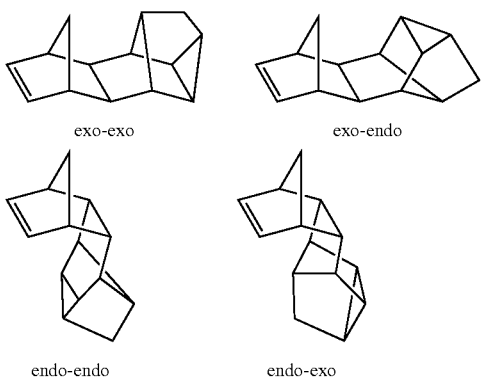

exo-exo    exo-endo endo-endo    endo-exo

In the present invention, all of these stereoisomers can be used as monomers. Further, as a monomer, one isomer may be used alone, or an isomer mixture containing 4 isomers in an arbitrary ratio may be used.

Above all, for the monomer used for the present invention, a monomer having a lot of endo-endo products or the endo-exo products is preferred because of the birefringence (δn) per a unit thickness close to zero. The total amount of the endo-endo products and endo-exo products is preferably 10 wt % or more, more preferably 30 wt % or more, even more preferably 50 wt % or more, and particularly preferably 70 wt % or more based on all monomers.

In the polymer (β) or the polymer (γ) (with the proviso that it is a hydrogenated product of the polymer (β)) (hereinafter they are collectively referred to as "copolymer (C) according to one embodiment of the invention" in some cases), the monomer other than MMD is not particularly limited as long as it is capable of ring-opening copolymerization with MMD. Examples of the monomer other than MMD include a monocyclic cycloolefin monomer, a norbornene-based monomer (a monomer containing a norbornene ring), and the like.

Examples of the monocyclic cycloolefin monomer include a cyclic monoolefin such as cyclobutene, cyclopentene, cyclohexene, cycloheptene and cyclooctene, and a derivative thereof (a monomer having a substituent on its ring, the same applies to the following); a cyclic diolefin such as cyclohexadiene and cyclooctadiene, and a derivative thereof; and the like.

Examples of the norbornene-based monomer include a bicyclic monomer such as bicyclo[2.2.1]hept-2-ene (trivial name: norbornene) and a derivative thereof; a tricyclic monomer such as tricyclo[4.3.0.1$^{2,5}$]deca-3,7-diene (trivial name: dicyclopentadiene) and a derivative thereof; a tetracyclic monomer such as 7,8-benzotricyclo[4.3.0.1$^{2,5}$]deca-3-ene (trivial name: methanotetrahydrofluorene, also referred to as "tetracyclo[7.4.0.0$^{2,7}$.1$^{10,13}$]trideca-2,4,6,11-tetraene), tetracyclo[4.4.0.1$^{2,5}$.1$^{7,10}$]dodeca-3-ene (trivial name: tetracyclododecene) and a derivative thereof; a monomer having not less than 5 rings such as 1,2,3,3a,4,6a-hexahydro-1,2,4-methenopentalene (trivial name: deltacyclene, hereinafter referred to as "DCL" in some cases) and a derivative thereof; and the like.

When these monomers have a substituent, the position of the substituent is not limited. Examples of the substituent include an alkyl group such as a methyl group and an ethyl group; an alkenyl group such as a vinyl group; an alkylidene group such as an ethylidene group and a propane-2-ylidene group; an aryl group such as a phenyl group; a hydroxy group; an acid anhydride group; a carboxyl group; an alkoxycarbonyl group such as a methoxycarbonyl group; and the like.

Among these monomers, the DCL [compound represented by the following formula (II)] is preferred because a copolymer having a higher refractive index and a lower birefringence can be easily obtained.

(II)

These monomers other than MMD can be used either alone or in combination.

In the copolymer (C) according to one embodiment of the invention of this patent application, the content of the repeating unit derived from the MMD is preferably 50 wt % or more, more preferably 70 wt % or more, and even more preferably 80 wt % or more based on the whole repeating unit. When the content of the repeating unit derived from the MMD is 50 wt % or more based on the whole repeating unit, a copolymer having a higher refractive index and a lower birefringence can be easily obtained.

The polymer (α) and the polymer (β) can be synthesized by ring-opening polymerization of a corresponding monomer in accordance with a known method using a metathesis polymerization catalyst.

The metathesis polymerization catalyst is not particularly limited. A known metathesis polymerization catalyst may be used. Examples of the metathesis polymerization catalyst include a catalyst system including a halide, a nitrate or an acetylacetone compound of a metal selected from ruthenium, rhodium, palladium, osmium, iridium, platinum, and the like, and a reducing agent; a catalyst system including a halide or an acetylacetone compound of a metal selected from titanium, vanadium, zirconium, tungsten and molybdenum, and an organoaluminum compound as a co-catalyst;

a Schrock-type or Grubbs-type living ring-opening metathesis polymerization catalyst (JP-A-7-179575, J. Am. Chem. Soc., 1986, 108, p. 733, J. Am. Chem. Soc., 1993, 115, p. 9858, and J. Am. Chem. Soc., 1996, 118, p. 100); a catalyst system including a complex having a metal such as chromium, molybdenum and tungsten and an imide group-containing ligand; and the like.

These metathesis polymerization catalysts can be used either alone or in combination. The amount of the metathesis polymerization catalyst to be used may be appropriately selected taking account of the polymerization conditions and the like, but is normally 0.000001 to 0.1 mol, and preferably 0.00001 to 0.01 mol based on 1 mol of the whole monomer.

A linear α-olefin having 4 to 40 carbon atoms such as 1-butene, 1-hexene and 1-decene can be used as a molecular weight modifier when carrying out ring-opening polymerization.

The linear α-olefin is normally added in an amount of 0.001 to 0.030 mol, preferably 0.003 to 0.020 mol, and more preferably 0.005 to 0.015 mol based on 1 mol of the whole monomer.

The ring-opening polymerization can be effected in an organic solvent. The organic solvent is not particularly limited as long as it is inert to the polymerization reaction. Examples of the organic solvent include an aromatic hydrocarbon-based solvent such as benzene, toluene and xylene; an aliphatic hydrocarbon-based solvent such as n-pentane, n-hexane and n-heptane; an alicyclic hydrocarbon-based solvent such as cyclohexane, methylcyclohexane, decalin and bicyclononane; a halogenated hydrocarbon-based solvent such as dichloroethane, chlorobenzene, dichlorobenzene and trichlorobenzene; and the like.

The polymerization temperature is not particularly limited, but is normally −50 to 250° C., preferably −30 to 200° C., and more preferably −20 to 150° C. The polymerization time is appropriately selected taking account of the polymerization conditions, but is normally 30 minutes to 20 hours, and preferably 1 to 10 hours.

The polymer (α) or the polymer (β) obtained in accordance with the above-described method is subjected to a hydrogenation reaction, so that a polymer (γ) corresponding them can be obtained, respectively.

This hydrogenation reaction can be effected by bringing the polymer (α) or the polymer (β) into contact with hydrogen under the presence of a hydrogenation catalyst in accordance with an ordinary method.

The hydrogenation catalyst may be a homogeneous catalyst or a heterogeneous catalyst.

Since a homogeneous catalyst is easily dispersed in a hydrogenation reaction solution, the amount of catalyst to be added can be reduced. In addition, since a homogeneous catalyst exhibits sufficient activity even when the temperature and the pressure are not increased, decomposition or gelation of the polymer (α), the polymer (β) and the polymer (γ) hardly occurs. Therefore, a homogeneous catalyst is preferably used from the viewpoint of cost and the quality of the product.

On the other hand, since a heterogeneous catalyst exhibits particularly excellent activity at a high temperature under high pressure, the polymer (α) or the polymer (β) can be hydrogenated within a short time. Moreover, a catalyst residue can be easily removed after completion of the hydrogenation reaction. Thus, the heterogeneous catalyst is preferably used from the viewpoint of production efficiency.

Examples of the homogeneous catalyst include a Wilkinson's complex [chlorotris(triphenylphosphine)rhodium(I)]; a catalyst including a combination of a transition metal compound and an alkylmetal compound, such as combinations of cobalt acetate/triethylaluminum, nickel acetylacetonate/triisobutylaluminum, titanocene dichloride/n-butyllithium, zirconocene dichloride/sec-butyllithium, tetrabutoxytitanate/dimethylmagnesium and the like; and the like.

Examples of the heterogeneous catalyst include a catalyst in which a metal such as Ni, Pd, Pt, Ru and Rh is supported on a support. Particularly, when the amount of impurities in the resulting hydrogenated product is to be reduced, it is preferable to use an adsorbent such as alumina and diatomaceous earth as the support.

The hydrogenation reaction is normally effected in an organic solvent. The organic solvent is not particularly limited as long as it is inert to the hydrogenation reaction. A hydrocarbon-based solvent is normally used as the organic solvent since a hydrocarbon-based solvent can easily dissolve the polymer (γ). Examples of the hydrocarbon-based solvent include an aromatic hydrocarbon-based solvent such as benzene, toluene and xylene; an aliphatic hydrocarbon-based solvent such as n-pentane, n-hexane and n-heptane; an alicyclic hydrocarbon-based solvent such as cyclohexane, methylcyclohexane, decalin and bicyclononane; and the like.

These organic solvents can be used either alone or in combination. In addition, a solvent used for a ring-opening polymerization reaction is normally also suitable as a solvent for a hydrogenation reaction, and therefore, after the hydrogenation catalyst is added to the ring-opening polymerization reaction solution, it can be subjected to the hydrogenation reaction.

The hydrogenation reaction can be effected in accordance with an ordinary method.

The hydrogenation ratio varies depending on the type of hydrogenation catalyst, and the reaction temperature. Therefore, when the polymer (α) or the polymer (β) has an aromatic ring, a residual ratio of the aromatic ring can be controlled by selection of the hydrogenation catalyst, adjustment of the reaction temperature or the like. For example, the unsaturated bonds of an aromatic ring can be allowed to remain to a certain extent or higher by controls such as selection of a hydrogenation catalyst, decrease of the reaction temperature, lowering of the hydrogen pressure and reduction of the reaction time.

A catalyst residue can be removed by a treatment such as centrifugation and filtration after completion of the hydrogenation reaction. In addition, a catalyst deactivation agent such as water and alcohol may be used, or an adsorbent such as activated clay and alumina may be added, as required.

The weight average molecular weight (Mw) of the polymer (B) according to one embodiment of the invention is preferably 10,000 to 300,000, and more preferably 20,000 to 200,000, and particularly preferably 30,000 to 150,000. If the weight average molecular weight (Mw) of the polymer is too low, the strength of the resin formed article possibly decreases. On the other hand, if the weight average molecular weight (Mw) of the polymer is too high, the formability of the forming material possibly decreases.

The molecular weight distribution (Mw/Mn) of the polymer (B) is not particularly limited, but is preferably 1 to 8, and more preferably 1 to 6.

When the molecular weight distribution of the polymer (B) is within the above range, a resin formed article having sufficient mechanical strength can be obtained.

The weight average molecular weight (Mw) and the number average molecular weight (Mn) of the polymer (B)

refer to standard polyisoprene-equivalent values determined by gel permeation chromatography (GPC) using cyclohexane as an eluent.

The polymer (B) according to one embodiment of the invention is a polymer having a high refractive index and a low birefringence because it has a repeating unit derived from the MMD.

The refractive index ($n_d$) of the polymer (B) according to one embodiment of the invention at 25° C. is preferably 1.540 or higher, and more preferably 1.545 to 1.560.

The birefringence ($\delta n$) per a unit thickness of the polymer (B) according to one embodiment of the invention is preferably −100 to +100, more preferably −85 to +80, and particularly preferably −60 to +60.

The refractive index and the birefringence per a unit thickness can be measured in accordance with the method described in Examples.

In the polymer (B) according to one embodiment of the invention, a melting point may be observed depending on a state of a measurement sample, but when DSC measurement is carried out using a measurement sample obtained by melting and subsequent cooling, a melting point is normally not observed. Thus, the polymer (B) according to one embodiment of the invention has an excellent transparency where respective polymer chains hardly align, even if the polymer chains have high-level tactic structures.

The light transmittance of light having a wavelength of 650 nm in the sheet formed article with a thickness of 3 mm obtained by using the polymer (B) according to one embodiment of the invention is preferably 88% or higher, more preferably 90% or higher, and even more preferably 92% or higher.

The glass transition temperature of the polymer (B) according to one embodiment of the invention is preferably 120 to 180° C., and more preferably 130 to 160° C.

When the glass transition temperature of the polymer (B) is within the above range, the balance between the formability of the forming material and the heat resistance of the resin formed article is improved.

In relation to the polymer (B) according to one embodiment of the invention, the glass transition temperature of the syndiotactic polymer tends to be within a range of 120 to 180° C. Thus, a polymer having a desired glass transition temperature can be efficiently obtained by a polymerization reaction using a known tungsten complex-based catalyst or the like from which a syndiotactic polymer is obtained.

As described above, since the polymer (B) according to one embodiment of the invention has a repeating unit derived from the MMD, it exhibits excellent transparency, and furthermore a high refractive index and a low birefringence. As the polymer (B) according to one embodiment of the invention, the polymer ($\gamma$) is preferred because of these superior properties, and the hydrogenated product of the polymer ($\alpha$) or the hydrogenated product of the copolymer of the MMD and the DCL is more preferred.

The polymer (B) according to one embodiment of the invention is useful as a resin component for an optical formed article.

2) Forming Material

The forming material according to one embodiment of the invention contains the copolymer (A) or the polymer (B) according to one embodiment of the invention. The forming material may contain a resin component other than the copolymer according to one embodiment of the invention and other components such as an additive as long as the effects according to one embodiment of the invention are not impaired.

Examples of the resin component other than the polymer according to one embodiment of the invention (hereinafter referred to as "another resin component" in some cases) include styrene-based polymers such as a styrene/butadiene block copolymer, a styrene/butadiene/styrene block copolymer, a styrene/isoprene block copolymer, a styrene/isoprene/styrene block copolymer and a hydrogenated product thereof, and a styrene/butadiene random copolymer.

When the forming material according to one embodiment of the invention contains another resin component, its content is normally 0.1 to 100 parts by weight, and preferably from 1 to 50 parts by weight based on 100 parts by weight of the copolymer according to one embodiment of the invention.

Examples of the additive include an antioxidant, a UV absorber, a light stabilizer, a near-infrared absorber, a plasticizer, an antistatic agent, an acid scavenger and the like.

Examples of the antioxidant include a phenol-based antioxidant, a phosphorus-based antioxidant, a sulfur-based antioxidant and the like.

Examples of the phenol-based antioxidant include 3,5-di-t-butyl-4-hydroxytoluene, dibutylhydroxytoluene, 2,2'-methylenebis(6-t-butyl-4-methylphenol), 4,4'-butylidenebis(3-t-butyl-3-methylphenol), 4,4'-thiobis(6-t-butyl-3-methylphenol), α-tocopherol, 2,2,4-trimethyl-6-hydroxy-7-t-butylchroman, tetrakis[methylene-3-(3',5'-di-t-butyl-4'-hydroxyphenyl)propionate]methane, [pentaerythritol tetrakis[3-(3,5-di-t-butyl-4-hydroxyphenyl)propionate]], and the like.

Examples of the phosphorus-based antioxidant include distearylpentaerythritol diphosphite, bis(2,4-di-t-butylphenyl)pentaerythritol diphosphite, tris(2,4-di-t-butylphenyl) phosphite, tetrakis(2,4-di-t-butylphenyl)-4,4'-biphenyl diphosphite, trinonylphenyl phosphite, and the like.

Examples of the sulfur-based antioxidant include distearyl thiodipropionate, dilauryl thiodipropionate and the like.

Examples of the UV absorber include a benzotriazole-based UV absorber, a benzoate-based UV absorber, a benzophenone-based UV absorber, an acrylate-based UV absorber, a metal complex-based UV absorber and the like.

Examples of the light stabilizer include a hindered amine-based light stabilizer.

Examples of the near-infrared absorber include a cyanine-based near-infrared absorber; a pyrylium-based infrared absorber; a squarylium-based near-infrared absorber; a croconium-based infrared absorber; an azulenium-based near-infrared absorber; a phthalocyanine-based near-infrared absorber; a dithiol metal complex-based near-infrared absorber; a naphthoquinone-based near-infrared absorber; an anthraquinone-based near-infrared absorber; an indophenol-based near-infrared absorber; an azide-based near-infrared absorber; and the like.

Examples of the plasticizer include a phosphoric acid triester-based plasticizer, a fatty acid monobasic acid ester-based plasticizer, a dihydric alcohol ester-based plasticizer, an oxy acid ester-based plasticizer and the like.

Examples of the antistatic agent include a fatty acid ester of a polyhydric alcohol and the like.

Examples of the acid scavenger include magnesium oxide, zinc stearate and the like.

The contents of these additives can be appropriately determined taking account of the objects. The contents are normally 0.001 to 5 parts by weight, and preferably 0.01 to 1 part by weight based on 100 parts by weight of the copolymer according to one embodiment of the invention.

The forming material can be obtained by mixing each component in accordance with an ordinary method.

Examples of the mixing method include a method of mixing each component in an appropriate solvent and a method of kneading the components in a molten state.

The components may be kneaded using a melt mixer such as a single-screw extruder, a twin-screw extruder, a Banbury mixer, a kneader and a feeder ruder. The kneading temperature is preferably 200 to 400° C., and more preferably 240 to 350° C. The components may be kneaded after adding each component at a time, or may be kneaded while adding the components stepwise.

After kneading, in accordance with an ordinary method, the resulting mixture is extruded in a shape of a rod, and cut using a strand cutter to have an appropriate length, so that it can be pelletized.

The forming material according to one embodiment of the invention contains the copolymer (A) or the polymer (B) according to one embodiment of the invention.

A resin formed article having excellent heat resistance, a high refractive index and a high Abbe's number can be obtained by using the forming material according to one embodiment of the invention containing the copolymer (A). Thus, the forming material according to one embodiment of the invention is suitably used as a forming material for an optical formed article such as a lens.

A resin formed article having excellent transparency and furthermore a high refractive index and a low birefringence can be efficiently obtained by using the forming material according to one embodiment of the invention containing the polymer (B). Thus, the forming material according to one embodiment of the invention is suitably used as a forming material for an optical formed article such as a lens.

In addition, the forming material containing the polymer (B) obtained by the method of kneading in a molten state normally has superior transparency where no melting point is observed by DSC measurement.

The forming material according to one embodiment of the invention is suitably used also for fuel application because of high density and high combustion heat.

3) Resin Formed Article

The resin formed article according to one embodiment of the invention can be obtained by forming the forming material according to one embodiment of the invention.

The forming method is not particularly limited. Examples of the forming method include injection forming, press forming, extrusion forming and the like. Above all, injection forming is preferred because a desired formed article can be precisely obtained, when the formed article is an optical member or the like.

The melting temperature employed during forming differs depending on the forming material to be used, but is normally 200 to 400° C., and preferably 210 to 350° C. When a die is used, the die temperature is normally 20° C. to (Tg+15)° C., preferably (Tg−30)° C. to (Tg+10)° C., and more preferably (Tg−20)° C. to (Tg+5) ° C., where the glass transition temperature of the forming material is defined as Tg.

Since the resin formed article according to one embodiment of the invention is obtained by forming the forming material according to one embodiment of the invention, it has excellent heat resistance and a high refractive index and a high Abbe's number.

The resin formed article according to one embodiment of the invention is suitably used as an optical member such as an optical lens, a prism, a light guide.

EXAMPLES

The present invention will be further described below by way of Examples and Comparative Examples in detail. Note that the present invention is not limited to the following examples. Hereinafter, the units "parts" and "%" respectively refer to "parts by weight" and "wt %" unless otherwise indicated, and the pressure refers to a gage pressure.

The various properties were measured in accordance with the method described below.

(1) Molecular Weight

The weight average molecular weight (Mw) of the copolymer (A) or the polymer (B) was measured as a standard polyisoprene-equivalent value by gel permeation chromatography (GPC) using cyclohexane as an eluent.

As the standard polyisoprene, a standard polyisoprene manufactured by Tosoh Corporation (Mw=602, 1390, 3920, 8050, 13800, 22700, 58800, 71300, 109000, 280000) was used.

The measurement was carried out using three columns (TSKgel G5000HXL, TSKgel G4000HXL and TSKgel G2000HXL) manufactured by Tosoh Corporation connected in series, under conditions of a flow rate of 1.0 mL/minute, a volume of the injected sample of 100 μL and a column temperature of 40° C.

(2) Glass Transition Temperature

The glass transition temperature (Tg) of the copolymer (A) or the polymer (B) was measured using a differential scanning calorimeter (product name: DSC6220SII, manufactured by NanoTechnology Inc.) at an increase rate of 10° C./min, in accordance with JIS K 6911.

(3) Refractive Index

The copolymer (A) or the polymer (B) was formed into a sheet with a thickness of 5 mm and left under an atmosphere at [glass transition temperature (Tg) of the addition copolymer −15]° C. for 20 hours to prepare a measurement sample.

For the resulting measurement sample, the refractive indexes ($n_d$, $n_c$, $n_F$) at 25° C. were measured using a precise refractometer (product name: KPR-200, light source=He lamp (587.6 nm), H2 lamp (656.3 nm, 486.1 nm), manufactured by Shimadzu Corporation).

Table 1 shows refractive indexes of light having a wavelength of 587.6 nm.

(4) Abbe's Number

The Abbe's number ($v_d$) was calculated using the refractive indices ($n_d$, $n_c$, $n_F$) at 25° C. obtained by measurement of the refractive indices, in accordance with the following equation (1).

$$v_d = (n_d - 1)/(n_F - n_c) \qquad (1)$$

In the equation (1), $n_d$, $n_c$ and $n_F$ represent refractive indices at wavelengths of 587.6 nm, 656.3 nm and 486.1 nm, respectively.

(5) Birefringence (δn) Per Unit Thickness

The copolymer (A) or the polymer (B) was formed into a shape of 35 mm×10 mm×1 mm. After fixing both ends of this sheet with clips, a 160 g weight was fixed to one clip. Subsequently, in an oven at [glass transition temperature (Tg) of the copolymer−15]° C., the sheet was stretched while the sheet was suspended with the clip having no fixed weight as the starting point for 10 minutes, to prepare a measurement sample.

For the resulting measurement sample, a retardation value of light having a wavelength of 650 nm at the center part of the measurement sample was measured using a birefringence meter (product name: KOBRA-CCD/X, manufactured by Oji Scientific Instruments Co., Ltd.) (the measured value is defined as "a").

In addition, a thickness at the center part of the measurement sample was measured (the measured value is defined as "b" (mm)) to determine a δn value in accordance with equation: δn=a×(1/b).

The closer the δn value is to zero, the lower the birefringence is. In addition, a sample with a birefringence generated in the stretching direction shows a positive value, and a sample with a birefringence generated in a direction perpendicular to the stretching direction shows a negative value.

(6) Analysis of Monomer (NMR)

A monomer was dissolved in deuterated chloroform (containing TMS) to prepare a measurement solution with a concentration of the monomer of 5%. Using this solution, $^1$H-NMR measurement was carried out at 40° C.

(Gas Chromatography)

The monomer was analyzed by gas chromatography (GC) under the following conditions.
Sample solution: 5% cyclohexane solution
Gas chromatographic analyzer: product name: 6850 series, manufactured by Agilent Technologies, Inc.
Column: product name: HP-1, 30 m, inner diameter: 0.32 mm, film thickness: 25 μm, manufactured by Agilent Technologies, Inc.
Split ratio: 70:1
Split flow rate: 140 mL/min
Injection temperature: 160° C.
Injection volume: 1.0 μL
Detection temperature: 250° C.
Flow rate of $N_2$: 2.0 mL/min
Temperature condition: holding at 40° C. for 6 minutes heating up to 240° C. at 10° C./min (7) Melting Point The melting point (Tm) of the polymer was measured using a differential scanning calorimeter (product name: DSC6220SII, manufactured by NanoTechnology Inc.) at an increase rate of 10° C./min, in accordance with JIS K 7121.

(8) Transparency

The resin composition was formed into a sheet having a thickness of 3 mm to prepare a measurement sample.

For the resulting measurement sample, the light transmittance (optical path length: 3 mm) of light having a wavelength of 650 nm was measured using an ultraviolet and visible spectrophotometer (product name: UV-VIS V570, manufactured by JASCO Corporation) to evaluate the transparency of the resin sheet. Subsequently, the measurement sample was heated (at 320° C. for 1 hour), and then the transparency of the heated resin sheet was similarly evaluated.

The transparency was evaluated in accordance with the following criteria.
"Good": the transmittance is 88% or higher.
"Bad": the transmittance is lower than 88%.

[Production Example 1] Synthesis of Alcohol Compound (1)

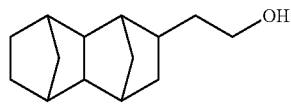

Alcohol compound (1)

Dicyclopentadiene (100 g) and 3-butene-1-ol (500 g) were added to a stainless steel autoclave, the inside of the system was replaced by nitrogen, sealed, then heated to 220° C. while stirring the whole content, and reacted for 1 hour. Subsequently, dicyclopentadiene (100 g) was further added to the reaction solution, the inside of the system was replaced by nitrogen, sealed, and then the same reaction operation was repeated twice.

The reaction solution was transferred to an autoclave equipped with a stirrer, to which 100 parts of cyclohexane and a diatomaceous earth-supported nickel catalyst (product name: T8400RL, nickel carrying ratio: 58%, manufactured by Clariant) (0.5 g) were added. The inside of the autoclave was replaced by hydrogen, and then hydrogenation reaction was carried out at 160° C. under a hydrogen pressure of 2.0 MPa for 2 hours.

After completion of the hydrogenation reaction, the reactant was pressure-filtered at 0.25 MPa using a pressure filter (product name: Funda Filter, manufactured by IHI Corporation) with diatomaceous earth (product name: Radiolite (registered trademark) #500, manufactured by SHOWA CHEMICAL INDUSTRY CO., LTD.) as a filtration bed to obtain a colorless transparent solution. Cyclohexane in the resulting solution was distilled off using a rotary evaporator, and the residue was distilled under reduced pressure (113 to 116° C., 0.013 kPa) to obtain 71 g of alcohol compound (1).

[Production Example 2] Synthesis of Monomer (1)

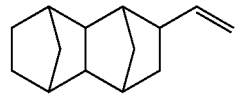

Monomer (1)

60 g of the alcohol compound (1) and 200 g of diethyl ether were added to a reactor whose inside had been replaced by nitrogen, into which 30 g of phosphorus tribromide was dropped while stirring the whole content at room temperature for 1 hour. After completion of the dropping, stirring was further continued for 23 hours to obtain a reaction solution. 400 g of toluene was added to the reaction solution, which was washed with 300 mL of saturated sodium bicarbonate aqueous solution three times, and then the organic layer was taken out by liquid separation.

Subsequently, while stirring the solution of the organic layer, 50 g of potassium t-butoxide was added to this solution at room temperature, and the stirring was further continued for 5 hours to obtain a reaction solution. 500 mL of toluene was added to the reaction solution, which was washed with 300 mL of 2 N hydrogen chloride aqueous solution three times, and then the organic layer was taken out by liquid separation.

Toluene in the organic layer was distilled off using a rotary evaporator, and the residue was distilled under reduced pressure (80 to 83° C., 0.13 kPa) to obtain 25 g of a monomer (1).

[Production Example 3] Synthesis of Monomer (2)

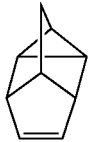

Monomer (2)

750 mL of dichloromethane, 150 g of norbornadiene, 14.8 g of cobalt catalyst [CoBr$_2$ (dppe)] and 23.5 g of zinc iodide were added to a reactor whose inside had been replaced by nitrogen, and the whole content was stirred at 25° C. Acetylene gas was blown into the resulting solution, to which 6.3 g of tetrabutylammonium borohydride was gradually added while stirring the whole content, and then the blowing of acetylene gas and the stirring were continued for 2 hours. Subsequently, 14.8 g of the cobalt catalyst was further added, and then the blowing of acetylene gas and the stirring were continued for 2 hours.

200 g of silica gel was added to the reaction solution, stirred for 10 minutes, and then impurities were filtered out. The filtrate was distilled off under reduced pressure to obtain 135 g of crude product.

The crude product was distilled under reduced pressure at 0.29 kPa at 24° C. to obtain 90 g of monomer (2) [deltacyclene (DCL)]. As a result of gas chromatography, the purity was 99%.

[Production Example 4] Synthesis of Monomer (3) (MMD)

200 parts of norbornadiene and 30 parts of rhodium-active carbon (5% Rh) were added to a reactor whose inside had been replaced by argon, which was heated to 110° C. while stirring the whole content, and the reaction was continued for 24 hours while maintaining the state.

After cooling the reaction solution, the solid content was filtered out to obtain 190 parts of crude product. The resulting crude product was distilled under reduced pressure (76° C., 80 Pa) to obtain 105 parts of monomer (3).

As a result of NMR measurement for the monomer (3), the monomer (3) was an isomer mixture including an exo-endo product and an endo-endo product, and their ratio (exo-endo product:endo-endo product) was estimated to be 86:14.

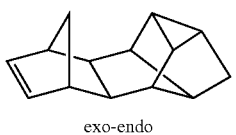
exo-endo

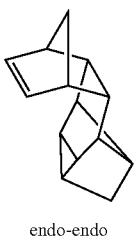
endo-endo

Example 1

A stirring bar, 30 mL of toluene, 174 mg of methylaluminoxane and 2 g of monomer (2) were put in a 100 mL autoclave whose inside had been replaced by nitrogen, to which a catalyst solution [1 mL of toluene solution containing 0.25 μmol of t-BuCpTi(N═C(t-Bu)$_2$)Cl$_2$] was added while stirring the whole content at 25° C. Immediately after adding the catalyst solution, ethylene gas was introduced so that the pressure was 0.2 MPa, to start addition polymerization reaction. The addition polymerization reaction was continued for 10 minutes while maintaining the temperature and the ethylene pressure in the autoclave. After depressurization, the content in the autoclave was transferred into a large amount of 2-propanol acidified by hydrochloric acid to precipitate a polymer. The resulting polymer (1) had a Tg of 166° C. and a refractive index of 1.553.

Example 2

A stirring bar, 8 g of toluene, 174 mg of methylaluminoxane, 1 g of monomer (1) and 1 g of monomer (2) were put in a 15 mL screw tube bottle whose inside had been replaced by nitrogen, to which a catalyst solution [1 mL of toluene solution containing 5 μmol of CpTi(N═C(t-Bu)$_2$)Cl$_2$] was further added to start addition polymerization reaction. The addition polymerization reaction was carried out while stirring the whole content at 25° C. for 120 hours, and then the content in the screw tube bottle was transferred into a large amount of 2-propanol acidified by hydrochloric acid to precipitate a polymer. The resulting polymer (2) had a weight average molecular weight (Mw) of 19,000 and a molecular weight distribution (Mw/Mn) of 1.9. The polymer (2) had a Tg of 179° C. and a refractive index of 1.558.

Example 3

A stirring bar, 20 g of cyclohexane, 38.4 mg of 1-hexene, 2.5 g of tetracyclododecene (TCD) and 2.5 g of monomer (2) were put in a 100 mL ampule bottle whose inside had been replaced by nitrogen, to which a catalyst solution [1 mL of toluene solution containing 6 μmol of benzylidene{1,3-bis (2,4,6-trimethylphenyl)-2-imidazolidinyl idene}dichloro (tricyclohexylphosphine) ruthenium] was further added, and the whole content was stirred at 60° C. for 3 hours to carryout ring-opening polymerization reaction. The conversion ratio of the monomer into the polymer was 100%.

Subsequently, 25 g of the resulting polymerization solution and 200 g of cyclohexane were transferred to an autoclave equipped with a stirrer, the inside of the autoclave was replaced by hydrogen, and then hydrogenation reaction was carried out at 150° C. under a hydrogen pressure of 4.5 MPa for 6 hours. As a result of $^1$H-NMR analysis, the hydrogenation ratio was 100%.

The resulting hydrogenation solution was dropped to a large amount of 2-propanol to precipitate a polymer. The polymer was taken by suction filtration, and then vacuum-dried at 60° C. for 24 hours. The resulting polymer (3) had a weight average molecular weight (Mw) of 16,000 and a molecular weight distribution (Mw/Mn) of 1.9. The polymer (3) had a Tg of 103° C. and a refractive index of 1.548.

Example 4

A stirring bar, 30 mL of toluene, 174 mg of methylaluminoxane and 2 g of monomer (3) were put in a 100 mL autoclave whose inside had been replaced by nitrogen, to which a catalyst solution [1 mL of toluene solution containing 0.25 μmol of CpTi(N═C(t-Bu)$_2$)Cl$_2$] was added while stirring the whole content at 25° C. Immediately after adding the catalyst solution, ethylene gas was introduced so that the pressure was 0.2 MPa, to start addition polymerization reaction. The addition polymerization reaction was continued for 10 minutes while maintaining the temperature and the ethylene pressure in the autoclave. After depressurization, the content in the autoclave was transferred into a large amount of 2-propanol acidified by hydrochloric acid to precipitate a polymer. The resulting polymer (4) had a weight average molecular weight (Mw) of 192,000 and a molecular weight distribution (Mw/Mn) of 1.64. The polymer (4) had a Tg of 188° C. and a refractive index of 1.552.

Comparative Example 1

A stirring bar, 30 mL of toluene, 174 mg of methylaluminoxane and 2 g of TCD were put in a 100 mL autoclave whose inside had been replaced by nitrogen, to which a catalyst solution [1 mL of toluene solution containing 0.25 µmol of [Me$_2$Si($\eta^5$-Me$_4$C$_5$)N(t-Bu)]TiCl$_2$ (CGC catalyst)] was added while stirring the whole content at 25° C. Immediately after adding the catalyst solution, ethylene gas was introduced so that the pressure was 0.5 MPa, to start addition polymerization reaction. The addition polymerization reaction was continued for 10 minutes while maintaining the temperature and the ethylene pressure in the autoclave. After depressurization, the content in the autoclave was transferred into a large amount of 2-propanol acidified by hydrochloric acid to precipitate a polymer. The resulting polymer (5) had a Tg of 140° C. and a refractive index of 1.544.

Comparative Example 2

A stirring bar, 40 g of cyclohexane, 0.05 g of 1-hexene, 6.5 g of methanotetrahydrofluorene, 3.0 g of tetracyclododecene and 0.5 g of norbornene were put in a 100 mL ampule bottle whose inside had been replaced by nitrogen, to which a catalyst solution [1 mL of toluene solution containing 6 µmol of benzylidene{1,3-bis(2,4,6-trimethylphenyl)-2-imidazolidinyl idene}dichloro(tricyclohexylphosphine) ruthenium] was further added, and the whole content was stirred at 60° C. for 3 hours to carryout ring-opening polymerization reaction. The conversion ratio of the monomer into the polymer was 100%.

Subsequently, 50 g of the obtained polymerization solution and 200 g of cyclohexane were transferred to an autoclave equipped with a stirrer, to which 0.5 g of diatomaceous earth-supported nickel catalyst (product name: T8400RL, nickel carrying ratio: 58%, manufactured b.JGC Catalysts and Chemicals Ltd.) was added. The inside of the autoclave was replaced by hydrogen, and then hydrogenation reaction was carried out at 190° C. under a hydrogen pressure of 4.5 MPa for 6 hours. As a result of $^1$H-NMR analysis, the hydrogenation ratio was 100%.

The diatomaceous earth-supported nickel catalyst in the hydrogenation solution was taken by suction filtration, and the resulting polymer solution was dropped to a large amount of 2-propanol to precipitate a polymer. The polymer was taken by suction filtration, and then vacuum-dried at 60° C. for 24 hours. The resulting polymer (6) had a weight average molecular weight (Mw) of 29,000 and a molecular weight distribution (Mw/Mn) of 2.0. The polymer (6) had a Tg of 143° C. and a refractive index of 1.535.

TABLE 1

|  | Example 1 | Example 2 | Example 3 | Example 4 | Comparative Example 1 | Comparative Example 2 |
| --- | --- | --- | --- | --- | --- | --- |
| Monomer α | Ethylene | Monomer (1) | TCD | Ethylene | Ethylene | Norbornene |
| Monomer β | Monomer (2) | Monomer (2) | Monomer (2) | Monomer (3) | TCD | TCD |
| Monomer γ | — | — | — | — | — | MTF |
| Polymerization method | Addition polymerization | Addition polymerization | Ring-opening polymerization | Addition polymerization | Addition polymerization | Ring-opening polymerization |
| Polymer | 1 | 2 | 3 | 4 | 5 | 6 |
| Tg | 166° C. | 179° C. | 103° C. | 189° C. | 140° C. | 143° C. |
| Refractive index | 1.553 | 1.558 | 1.548 | 1.552 | 1.544 | 1.535 |
| Abbe's number | 55 | 55 | 55 | 55 | 55 | 55 |
| Birefringence per a unit thickness (δn) | 20 | — | 60 | 20 | 20 | 120 |

Table 1 shows the followings.

Although all of the copolymers of Examples 1, 2 and 4 and Comparative Example 1 are addition polymers, the copolymers of Examples 1, 2 and 4 have higher glass transition temperatures and higher refractive indexes compared to the copolymer of Comparative Example 1.

Although both the copolymers of Example 3 and Comparative Example 2 are ring-opening polymers, the copolymer of Example 3 has a higher refractive index compared to the copolymer of Comparative Example 2.

In addition, the copolymers of Examples have relatively low birefringence per a unit thickness and is excellent in low birefringence.

[Production Example 5] Synthesis of DCL [Monomer (4)]

750 mL of dichloromethane, 150 g of norbornadiene, 14.8 g of cobalt catalyst [CoBr$_2$ (dPPe)] and 23.5 g of zinc iodide were put in a reactor whose inside had been replaced by nitrogen, and the whole content was stirred at 25° C. Acetylene gas was blown into the resulting solution, to which 6.3 g of tetrabutylammonium borohydride was gradually added while stirring the whole content, and then the blowing of the acetylene gas and the stirring were continued for 2 hours. Subsequently, 14.8 g of the cobalt catalyst was further added, and then the blowing of the acetylene gas and the stirring were continued for 2 hours.

200 g of silica gel was added to the reaction solution, stirred for 10 minutes, and then insolubles were filtered out. The filtrate was distilled off under reduced pressure to obtain 135 g of crude product.

The crude product was distilled under reduced pressure at 0.3 kPa at 24° C. to obtain 90 g of monomer (4). As a result of gas chromatography, the purity was 99%.

[Production Example 6] Synthesis of MMD [Monomer (5)] by Reaction (α)

43 g of dicyclopentadiene and 250 g of monomer (4) were put in a stainless steel autoclave, the inside of the system was replaced by nitrogen, then sealed, and heated to 220° C. while stirring the whole content, and the reaction was continued while maintaining the state for 2 hour.

Figure 2:
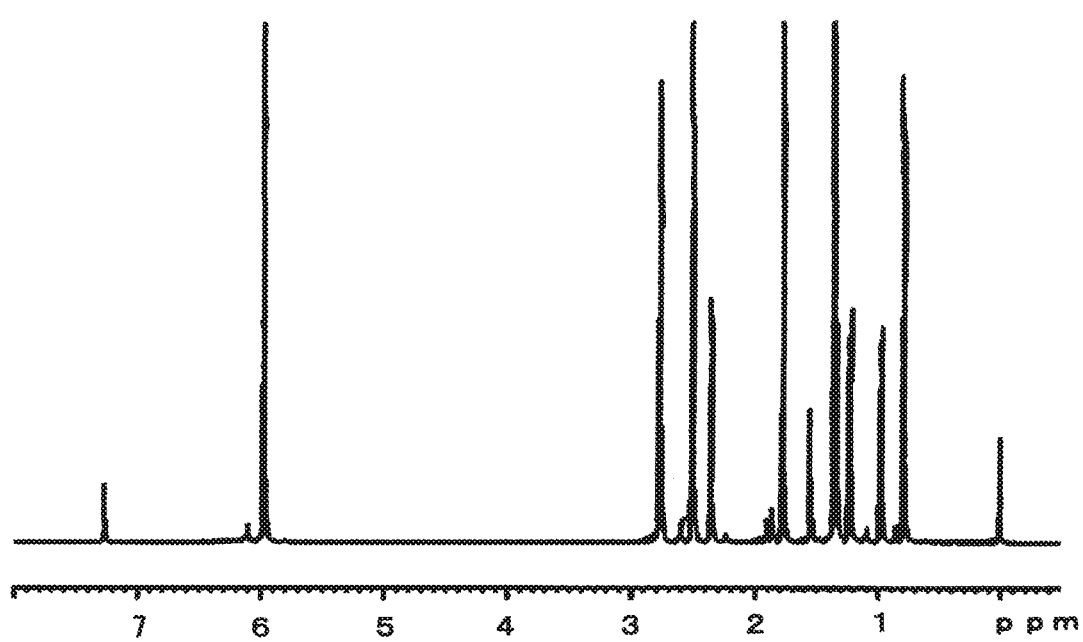
FIG. 2 illustrates a $^1$H-NMR chart (with integral representation) of the monomer (5). The abscissa represents values of chemical shift (ppm) and the ordinate represents peak intensities.
Figure 3:
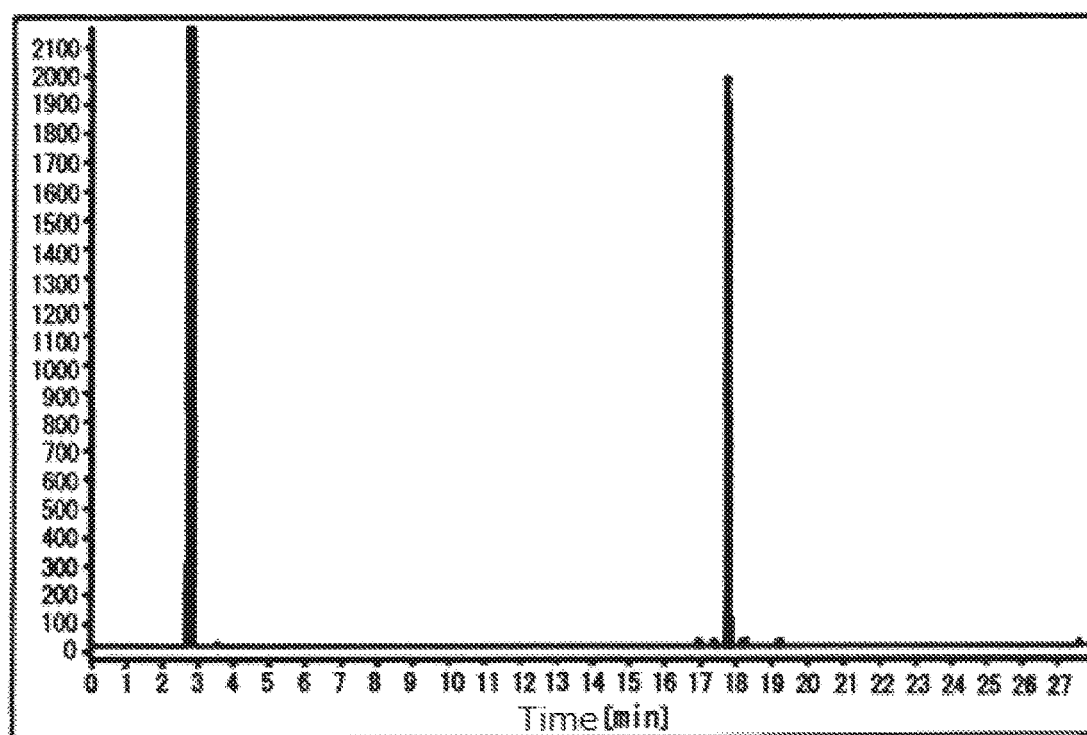
FIG. 3 illustrates a GC chart of the monomer (5). The abscissa represents time (min), and the ordinate represents peak intensities.

After cooling the reaction solution, 61 g of monomer (5) was obtained by distillation under reduced pressure (57 to 61° C., 40 Pa). NMR charts of the monomer (5) are shown in FIGS. 1 and 2. Further, a GC chart of the monomer (5) is shown in FIG. 3.

As shown in the NMR chart of the monomer (5), the monomer (5) was an isomer mixture including an endo-exo product and an exo-endo product, and their ratio (endo-exo product:exo-endo product) was estimated to be 97:3 (The isomer was identified with reference to J. Am. Chem. Soc. 1972, 94, 5446. The above description also applies to Production Example 6.).

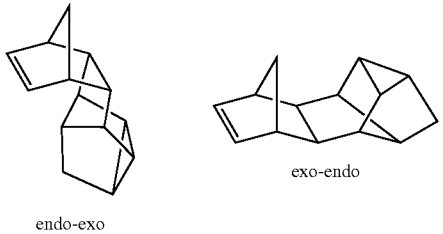

endo-exo    exo-endo

[Production Example 7] Synthesis of MMD [Monomer (6)] by Reaction (β)

200 parts of norbornadiene and 30 parts of rhodium-active carbon (5% Rh) were added to a reactor whose inside had been replaced by argon, which was heated to 110° C. while stirring the whole content, and the reaction was continued for 24 hours while maintaining the state.

Figure 4:
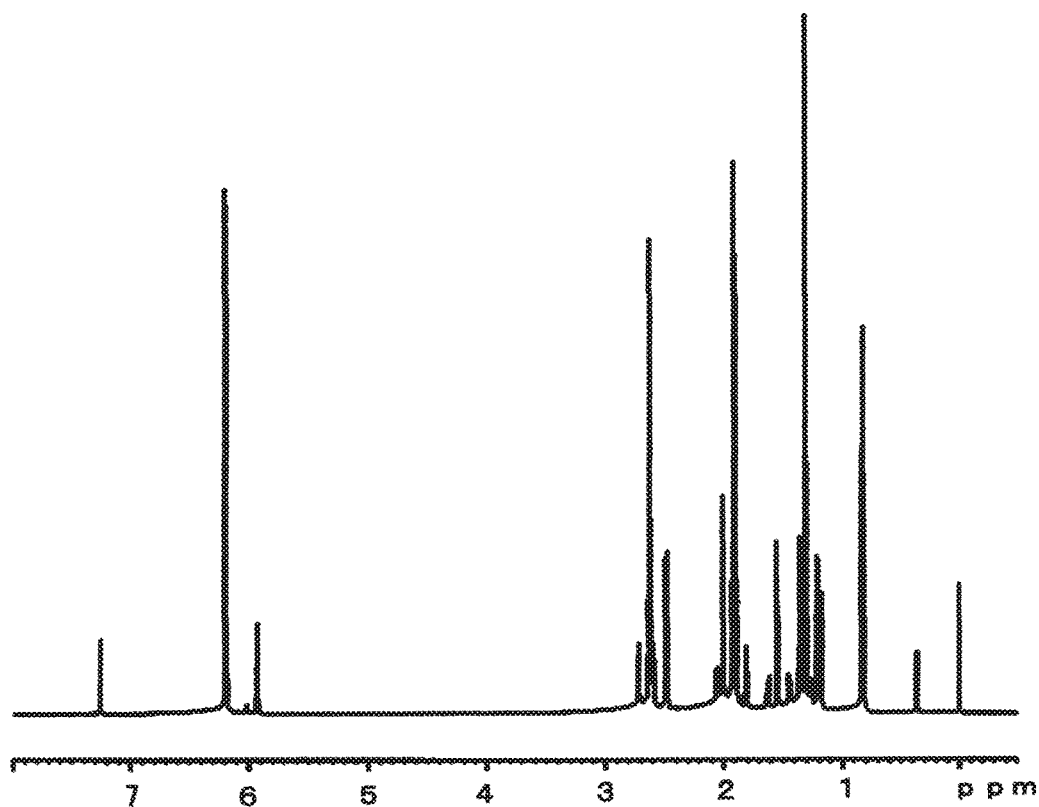
FIG. 4 illustrates a $^1$H-NMR chart (without integral representation) of a monomer (6). The abscissa represents values of chemical shift (ppm), and the ordinate represents peak intensities.
Figure 5:
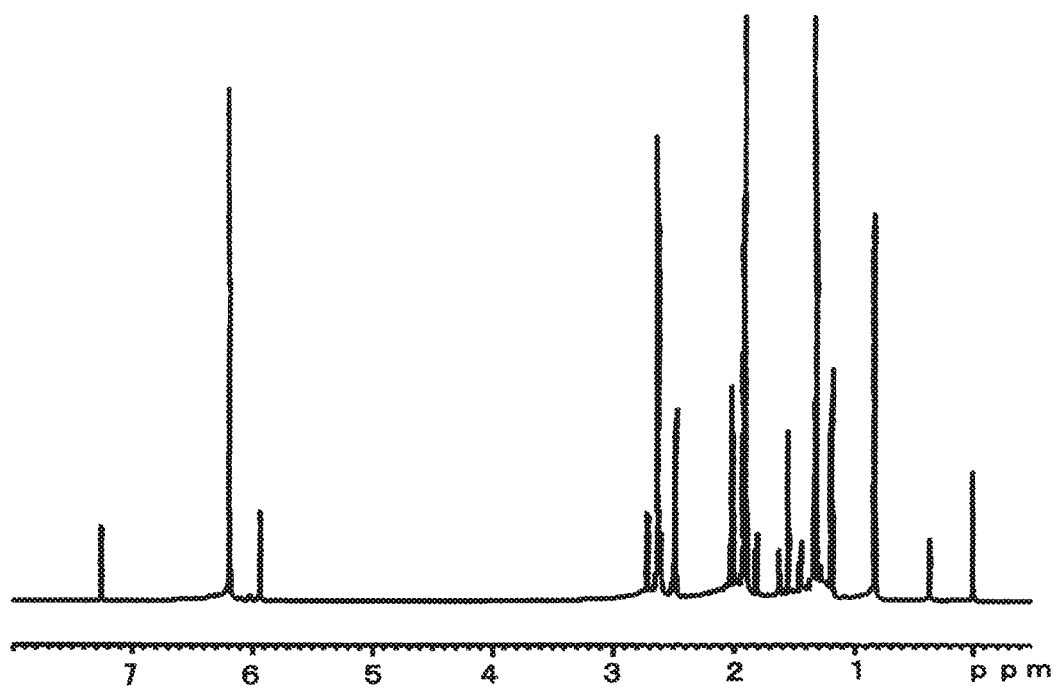
FIG. 5 illustrates a $^1$H-NMR chart (with integral representation) of the monomer (6). The abscissa represents values of chemical shift (ppm) and the ordinate represents peak intensities.
Figure 6:
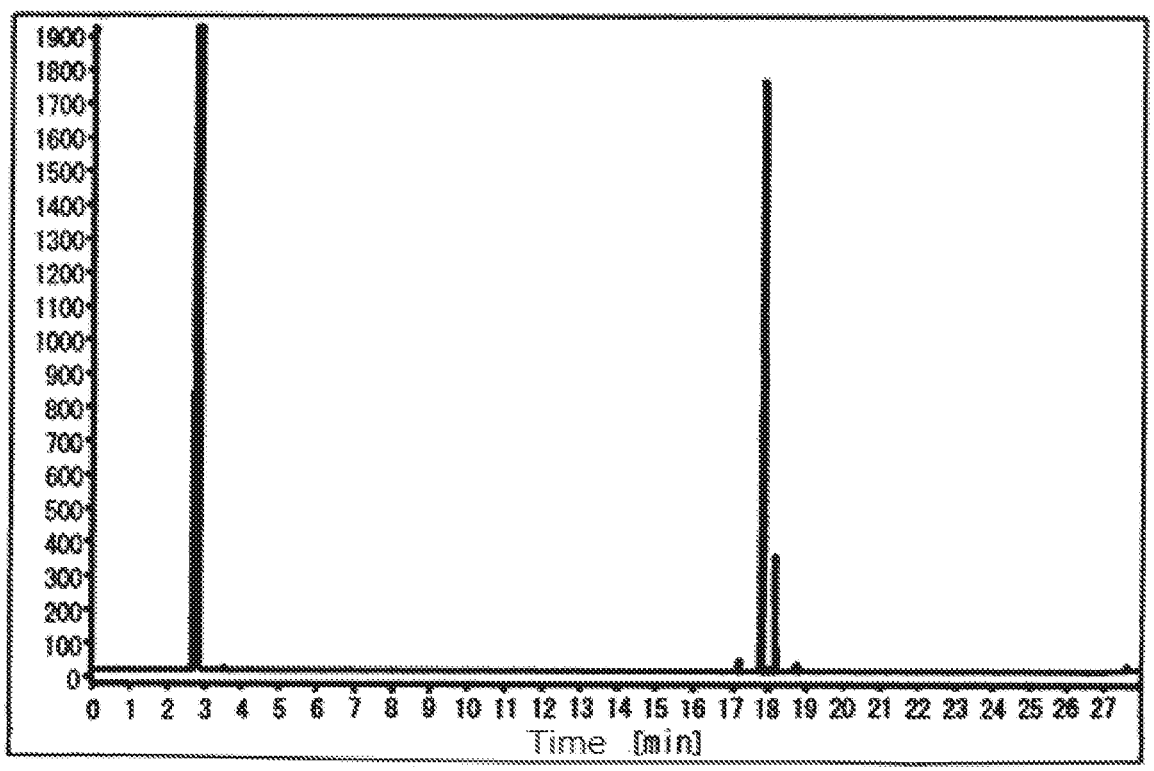
FIG. 6 illustrates a GC chart of the monomer (6). The abscissa represents time (min), and the ordinate represents peak intensities.

After cooling the reaction solution, the solid content was filtered out to obtain 190 parts of crude product. The resulting crude product was distilled under reduced pressure (76° C., 80 Pa) to obtain 105 parts of monomer (6). NMR charts of the monomer (6) are shown in FIGS. 4 and 5. Further, a gas chromatography (GC) chart of the monomer (6) is shown in FIG. 6.

As shown in the NMR chart of the monomer (6), the monomer (6) was an isomer mixture including an exo-endo product and an endo-endo product, and their ratio (exo-endo product:endo-endo product) was estimated to be 86:14.

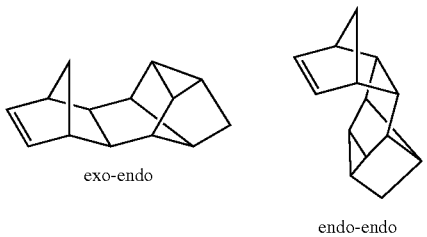

exo-endo    endo-endo

Monomers used in the following Examples and Comparative Examples are shown below.

Monomer (4): DCL
Monomer (5): MMD [Reaction (A)]
Monomer (6): MMD [Reaction (B)]
MTF: Methanotetrahydrofluorene
TCD: Tetracyclododecene
NB: Norbornene

Example 5

2.0 parts of monomer (5) (1% based on the total amount of the monomers to be used for polymerization), 785 parts of dehydrated cyclohexane, 15.0 parts of molecular weight modifier (1-hexene), 0.98 part of n-hexane solution of diethylaluminum ethoxide (concentration: 19%), and 11.7 parts of toluene solution of tungsten (phenylimido) tetrachloride tetrahydrofuran (concentration: 2.0%) (hereinafter referred to as "W catalyst (1)" in some cases) were put in a polymerization reactor whose inside had been dried and replaced by nitrogen, which was stirred at 50° C. for 10 minutes.

Subsequently, 198.0 parts of the monomer (2) was continuously dropped to the polymerization reactor for 150 minutes while maintaining the whole content at 50° C. and stirring. After completion of the dropping, the stirring was continued for 30 minutes, and then 4 parts of isopropyl alcohol was added to terminate the polymerization reaction. As a result of measuring the polymerization solution by gas chromatography, the conversion ratio of the monomer into the polymer was 100%, the polymer had a weight average molecular weight (Mw) of 52,000 and a molecular weight distribution (Mw/Mn) of 2.9.

Subsequently, 300 parts of the resulting polymerization solution was transferred to an autoclave equipped with a stirrer, to which 0.0043 part of chlorohydridocarbonyltris (triphenylphosphine) ruthenium was added, and hydrogenation reaction was carried out at 160° C. under a hydrogen pressure of 4.5 MPa for 4 hours.

After completion of the hydrogenation reaction, the resulting solution was poured into a large amount of isopropanol to precipitate a polymer. The polymer was taken by filtration, to which 0.5 part of antioxidant [pentaerythrityl-tetrakis[3-(3,5-di-t-butyl-4-hydroxyphenyl)propionate] (product name: "IRGANOX (Registered trademark) 1010" manufactured by BASF SE)] was subsequently added, which was put in an aluminum vat, and dried in a vacuum dryer (220° C., 133 Pa) for 6 hours to obtain a polymer (1).

The polymer (1) was slightly whitish. As a result of DSC measurement for the polymer (1), the glass transition temperature (Tg) was 178° C., and a melting point (Tm) was observed at 299° C. When the polymer (1) was subsequently heated at 320° C. under nitrogen atmosphere for 1 hour, no melting point was observed by DSC measurement.

Various measurements were carried out for the polymer (1). The results are shown in Table 2.

Example 6

A polymer (2) was obtained in the same manner as Example 1 except that a monomer mixture (monomer (5): monomer (4)=9:1) was used instead of the monomer (5) and the amount of the molecular weight modifier (1-hexene) was 20.0 parts.

In the polymerization reaction, the conversion ratio of the monomer into the polymer was 100%, and the weight average molecular weight (Mw) of the polymer before the hydrogenation reaction was 35,000, and the molecular weight distribution (Mw/Mn) was 3.4.

As a result of the DSC measurement for the polymer (2), no melting point was observed.

Various measurements were carried out for the polymer (2). The results are shown in Table 2.

Example 7

A polymer (3) was obtained in the same manner as Example 1 except that the monomer (6) was used instead of the monomer (5) and the amount of the molecular weight modifier (1-hexene) was 7.0 parts.

In the polymerization reaction, the conversion ratio of the monomer into the polymer was 100%, and the weight average molecular weight (Mw) of the polymer before the hydrogenation reaction was 26,000, and the molecular weight distribution (Mw/Mn) was 4.0.

The polymer (3) was slightly whitish. As a result of DSC measurement for the polymer (3), the glass transition temperature (Tg) was 143° C., and a melting point (Tm) was observed at 225° C. When the polymer (3) was subsequently heated at 320° C. under nitrogen atmosphere for 1 hour, no melting point was observed by DSC measurement.

Various measurements were carried out for the polymer (3). The results are shown in Table 2.

Example 8

0.05 part of polymerization catalyst [(1,3-dimesitylimidazolidine-2-ylidene) (tricyclohexylphosphine) benzylidene ruthenium dichloride] (hereinafter referred to as "Ru catalyst" in some cases), 100 parts of toluene, 20 parts of monomer (6) and 1.4 parts of molecular weight modifier (1-hexene) were added to a glass reactor whose inside had been replaced with nitrogen, and the whole content was stirred at 60° C. for 1 hour to carry out the ring-opening polymerization reaction. The conversion ratio of the monomer into the polymer was 100%, and the polymer had a weight average molecular weight (Mw) of 18,000 and a molecular weight distribution (Mw/Mn) of 1.5.

Subsequently, 300 parts of the resulting polymerization solution was transferred to an autoclave equipped with a stirrer, to which 0.0043 part of chlorohydridocarbonyltris (triphenylphosphine) ruthenium was added to carry out hydrogenation reaction at 160° C. under a hydrogen pressure of 4.5 MPa for 4 hours.

After completion of the hydrogenation reaction, the resulting solution was poured into a large amount of isopropanol to precipitate a polymer. The polymer was taken by filtration, to which 0.5 part of antioxidant [pentaerythrityl-tetrakis[3-(3,5-di-t-butyl-4-hydroxyphenyl)propionate] (product name: "IRGANOX (registered trademark) 1010", manufactured by BASF SE)] was subsequently added, which was put in an aluminum vat, and dried in a vacuum dryer (220° C., 133 Pa) for 6 hours to obtain a polymer (4).

The polymer (4) was slightly whitish. As a result of DSC measurement for the polymer (4), the glass transition temperature (Tg) was 135.6° C., and a melting point (Tm) was observed at 218° C. When the polymer (4) was subsequently heated at 320° C. under nitrogen atmosphere for 1 hour, no melting point was observed by DSC measurement.

Various measurements were carried out for the polymer (4). The results are shown in Table 2.

Comparative Example 3

7 parts of norbornene-based monomer mixture (MTF/TCD/NB=65/30/5) (1% based on the total amount of the monomers used for the polymerization), 1,600 parts of dehydrated cyclohexane, 0.6 part of 1-hexene, 1.3 parts of diisopropylether, 0.33 part of isobutyl alcohol, and 0.84 part of triisobutyl aluminum and 30 parts of cyclohexane solution containing 0.66% of tungsten hexchloride (hereinafter referred to as "W catalyst (2)" in some cases) were put in a polymerization reactor dried and replaced by nitrogen, which was stirred at 55° C. for 10 minutes.

Subsequently, 693 parts of the monomer mixture and 72 parts of cyclohexane solution containing 0.77% of tungsten hexachloride were continuously dropped to the polymerization reactor for 150 minutes, respectively, while maintaining the reaction system at 55° C. and stirring. After completion of the dropping, the stirring was further continued for 30 minutes, and then 1.0 part of isopropyl alcohol was added to terminate the polymerization reaction. As a result of measuring the polymerization solution by gas chromatography, the conversion ratio of the monomer into the polymer was 100%, the polymer had a weight average molecular weight (Mw) of 24,000 and a molecular weight distribution (Mw/Mn) of 2.2.

Subsequently, 300 parts of the resulting polymerization solution was transferred to an autoclave equipped with a stirrer, to which 100 parts of cyclohexane and 2.0 parts of diatomaceous earth-supported nickel catalyst (product name: "T8400RL", nickel carrying ratio: 58%, manufactured b.JGC Catalysts and Chemicals Ltd.) were added. The inside of the autoclave was replaced by hydrogen, and then hydrogenation reaction was carried out at 180° C. under a hydrogen pressure of 4.5 MPa for 6 hours.

After completion of the hydrogenation reaction, the reactant was pressure-filtered at 0.25 MPa using a pressure filter (product name: "Funda Filter", manufactured by IHI Corporation) with diatomaceous earth (product name: "Radiolite (registered trademark) #500" manufactured by SHOWA CHEMICAL INDUSTRY CO., LTD.) as a filtration bed to obtain a colorless transparent solution.

Subsequently, to the resulting solution, 0.5 part of antioxidant [pentaerythrityl-tetrakis[3-(3,5-di-t-butyl-4-hydroxyphenyl)propionate] (product name: "IRGANOX (registered trademark) 1010" manufactured by BASF SE)] was added based on 100 parts of the hydrogenated polymer.

This solution was filtered by a filter (product name: "Zeta Plus (registered trademark) 30H", pore diameter: 0.5 to 1 μm, manufactured by CUNO Filter Systems), and then the filtrate was filtered with a metal fiber filter (pore diameter: 0.4 μm, manufactured by NICHIDAI CO., LTD.) to remove contaminants.

Subsequently, for the filtrate obtained above, cyclohexane and other volatile components were removed from the solution at 260° C. and 1 kPa or lower using a cylindrical concentration dryer (manufactured by Hitachi, Ltd.), and then the hydrogenated polymer was extruded in a molten strand state from a die directly connected to the concentrator, cooled with water, and then cut with a pelletizer (product name: "OSP-2" manufactured by OSADA SEISAKUSHO) to obtain a pellet of the hydrogenated polymer [polymer (5)].

Various measurements were carried out for the polymer (5). The results are shown in Table 2.

Comparative Example 4

Polymerization reaction was carried out in the same manner as Comparative Example 1 except that MTF was used instead of the norbornene-based monomer mixture. The resulting polymer had a weight average molecular weight (Mw) of 26,000 and a molecular weight distribution (Mw/Mn) of 2.2. As a result of DSC measurement, no melting point was observed in this polymer.

Subsequently, the resulting polymer was hydrogenated in the same manner as the hydrogenation reaction in Comparative Example 1 to obtain a pellet of the hydrogenated polymer [polymer (6)].

Various measurements were carried out for the polymer (6). The results are shown in Table 2.

TABLE 2

|  |  | Example 5 | Example 6 | Example 7 | Example 8 | Comparative Example 3 | Comparative Example 4 |
|---|---|---|---|---|---|---|---|
| Ratio of monomer (%) | MMD (Monomer (6)) | 100 | 90 | — | — | — | — |
|  | MMD (Monomer (5)) | — | — | 100 | 100 | — | — |
|  | DCL (Monomer (4)) | — | 10 | — | — | — | — |
|  | MTF | — | — | — | — | 65 | 100 |
|  | TCD | — | — | — | — | 35 | — |
|  | NB | — | — | — | — | 5 | — |
| Catalyst for polymerization reaction |  | W catalyst (1) | W catalyst (1) | W catalyst (1) | Ru catalyst | W catalyst (2) | W catalyst (2) |
| Glass transition temperature Tg (° C.) |  | 178 | 163 | 143 | 135.6 | 149 | 160 |
| Refractive index nd |  | 1.549 | 1.550 | 1.550 | 1.550 | 1.5350 | 1.5345 |
| Abbe's number vd |  | 56 | 56 | 56 | 56 | 56 | 56 |
| Birefringence per a unit thickness (δn) |  | 50 | 50 | 80 | 80 | 120 | 110 |
| Transparency (before heating) |  | Bad | Good | Bad | Bad | Good | Good |

Table 2 shows the followings.

The polymers (1) to (4) of Examples 5 to 8 are polymers having high refractive index and low birefringence. In addition, although polymers (1), (3) and (4) immediately after the synthesis are whitish and inferior in transparency, the transparency is improved by heat treatment.

On the other hand, the polymers (5) and (6) of Comparative Examples 3 and 4 are excellent in transparency but their refractive indexes are not high, and they are inferior in low birefringence.

The invention claimed is:

1. A copolymer (A); which is
a copolymer obtained by copolymerizing one or plural cycloolefin monomers and one or plural acyclic olefin monomers, or
a copolymer obtained by copolymerizing two or more cycloolefin monomers,
  wherein the glass transition temperature (Tg) of the copolymer is 100° C. or higher and 179° C. or lower, the refractive index of the copolymer is 1.545 or higher, and the Abbe's number of the copolymer is 50 or larger, and
  at least one of the cycloolefin monomers is a monomer represented by the following formula (I)

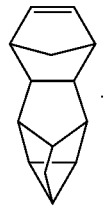

(I)

2. The copolymer (A) according to claim 1, wherein at least one of the acyclic olefin monomers is an α-olefin-based monomer having 2 to 18 carbon atoms.

3. The copolymer (A) according to claim 1, wherein at least one of the acyclic olefin monomers is ethylene.

* * * * *